(12) United States Patent
Yajima et al.

(10) Patent No.: US 11,999,761 B2
(45) Date of Patent: Jun. 4, 2024

(54) IODINE-CONTAINING COMPOUND

(71) Applicants: OCHANOMIZU UNIVERSITY, Tokyo (JP); DAIKIN INDUSTRIES, LTD., Osaka (JP)

(72) Inventors: Tomoko Yajima, Tokyo (JP); Tadashi Kanbara, Osaka (JP); Tsuyoshi Noguchi, Osaka (JP)

(73) Assignees: OCHANOMIZU UNIVERSITY, Tokyo (JP); DAIKIN INDUSTRIES, LTD., Osaka (JP)

( * ) Notice: Subject to any disclaimer, the term of this patent is extended or adjusted under 35 U.S.C. 154(b) by 804 days.

(21) Appl. No.: 17/090,455

(22) Filed: Nov. 5, 2020

(65) Prior Publication Data
US 2021/0054004 A1 Feb. 25, 2021

Related U.S. Application Data

(63) Continuation of application No. PCT/JP2019/018114, filed on Apr. 26, 2019.

(30) Foreign Application Priority Data

May 7, 2018 (JP) ................. 2018-089484

(51) Int. Cl.
C07C 69/65 (2006.01)
C07C 69/653 (2006.01)
C07F 7/21 (2006.01)
C08F 293/00 (2006.01)

(52) U.S. Cl.
CPC ............ C07F 7/21 (2013.01); C08F 293/005 (2013.01); *C08F 2438/00* (2013.01)

(58) Field of Classification Search
CPC ......... C07C 69/65; C07F 7/21; C08F 293/005
See application file for complete search history.

(56) References Cited

U.S. PATENT DOCUMENTS

| 2011/0275775 A1 | 11/2011 | Goto et al. |
| 2014/0303334 A1 | 10/2014 | Goto et al. |
| 2017/0306073 A1 | 10/2017 | Goto et al. |

FOREIGN PATENT DOCUMENTS

| CN | 102911054 A | 2/2013 |
| EP | 0 947 527 A1 | 10/1999 |
| JP | 2001-233806 A | 8/2001 |
| JP | 2004-323800 A | 11/2004 |
| JP | 2009-215376 A | 9/2009 |
| JP | 2012-122033 A | 6/2012 |
| JP | 2014-111798 A | 6/2014 |
| JP | 2016-053097 A | 4/2016 |
| KR | 10-2016-0096747 A | 8/2016 |
| WO | 2013/027419 A | 2/2013 |

OTHER PUBLICATIONS

Jeff Tonnar at el., "Synthesis of Poly(vinyl acetate)-block-poly (dimethylsiloxane)-block-poly (vinyl acetate) Copolymers by Iodine Transfer Polymerization in Miniemulsion", Macromolecular Symposia, 2009, vol. 281, 20-30, 11 pages.
Maki Yasuo at el., "Synthesis of Fluorine Containing DL Alanine Derivatives", Synthetic Organic Chemistry, 1976, vol. 34, No. 10, pp. 722-725, 5 pages.
Tomoko Yajima et al., "Photoinduced radical hydroperfluoroalkylation and the synthesis of fluorinated amino acids and peptides", Journal of Fluorine Chemistry, 2013, vol. 150, 7 pages.
Tomoko Yajima et al., "Photoinduced addition and addition-elimination reactions of perfluoroalkyl iodides to electron-deficient olefins" Tetrahedron, 2012, vol. 68, pp. 6856-6861, 6 pages.
International search report for PCT/JP2019/018114 dated Aug. 6, 2019.
International Preliminary Report on Patentability with a Translation of Written Opinion in International Application No. PCT/JP2019018114, dated Nov. 10, 2020.
E Pouget et al., "Synthesis of Poly(styrene)-b-poly(dimethylsiloxane)-b-poly(styrene) Triblock Copolymers by Iodine Transfer Polymerization in Miniemulsion", Macromolecules, vol. 39, 2006, pp. 6009-6016 (9 pages total).
Farrokhi et al., "ω-Iodinated poly(dimethylsiloxane) as a chain transfer agent in iodine transfer radical polymerization of vinyl acetate and dibutyl maleate: synthesis and structural characterization", Journal of Polymer Research, vol. 23, No. 122, May 31, 2016, XP055885588 (11 pages total).
Peralta-Hernández et al., "A practical free-radical approach to 1,4-dicarbonyl compounds", TETRAHEDRON, vol. 71, No. 15, Feb. 26, 2015, pp. 2234-2240, XP029146806 (7 pages total).
Tonnar et al., "Synthesis of poly(vinyl acetate)-b-poly(dimethylsiloxane)-b-poly( vinyl acetate) triblock copolymers by iodine transfer polymerization", European Polymer Journal, vol. 44, No. 2, Dec. 4, 2007, pp. 318-328, XP022442597 (11 pages total).
Xiao et al., "Organocatalyzed Living Radical Polymerization via in Situ Halogen Exchange of Alkyl Bromides to Alkyl Iodides", Macromolecules, vol. 50, No. 5, Feb. 28, 2017, pp. 1882-1891, XP055885537 (10 pages total).
Tanishima et al., "Macromolecular Architectures Designed by Living Radical Polymerization with Organic Catalysts", Polymers, vol. 6, No. 2, Jan. 27, 2014, pp. 311-326, XP055416669 (16 pages total).
Extended European Search Report dated Feb. 10, 2022 from the European Patent Office in counterpart EP Application No. 19800546.4.

*Primary Examiner* — Caixia Lu
(74) *Attorney, Agent, or Firm* — Sughrue Mion, PLLC

(57) ABSTRACT

An iodine compound represented by formula (3) and a polymerization inhibitor including the iodine compound, wherein $R^{21}$ to $R^{25}$ are as defined herein, $X^1$ is an n1-valent group, and n1 is an integer of 1 to 10:

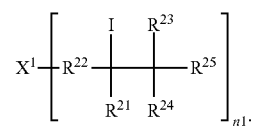

2 Claims, No Drawings

IODINE-CONTAINING COMPOUND

This is a Continuation application under 37 C.F.R. § 1.53(b) of International Application No. PCT/JP2019/018114 filed Apr. 26, 2019, which claims priority from Japanese Patent Application No. 2018-089484 filed May 7, 2018. The above noted applications are incorporated herein by reference in their respective entireties.

TECHNICAL FIELD

The present disclosure relates to an iodine-containing compound.

BACKGROUND ART

Conventionally, living radical polymerization using an iodine-containing compound has been known (Patent Literature 1).

CITATION LIST

Patent Literature

Patent Literature 1: International Publication No. WO 2013/027419

SUMMARY OF THE INVENTION

Problem to be Solved by the Invention

Living radical polymerization as described in Patent Literature 1 is advantageous in that the molecular weight can be controlled and a polymer can be obtained without using a metal or a compound containing a metal as a catalyst. However, in the polymerization using such an iodine-containing compound, there are few kinds of polymerization initiator species as a starting material, and a new polymerization initiator species is desired.

Accordingly, it is an object of the present disclosure to provide an iodine-containing compound that can be used as a polymerization initiator species for living radical polymerization.

Means to Solve the Problem

The present disclosure includes the following embodiments [1] to [10].

[1] A compound represented by any of the following formulae (1) to (4):

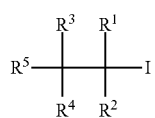
(1)

wherein
$R^1$ is H, F, Cl, $CH_3$, $CF_3$, or $O(CF_2)_{p1}F$;
$R^2$ is $-COOR^6$, $-PO(OR^6)_2$, $-SO_3-R^6$, $-SO_2-R^6$, $-SO-R^6$, -phenylen-$R^6$, or $-CONR^{10}_2$;
$R^3$ is H or F;
$R^4$ is H, F, an aryl group, $-COOR^9$, or an alkyl group optionally substituted with fluorine;
$R^5$ is H, F, an aryl group, $-COOR^9$, or an alkyl group optionally substituted with fluorine;
$R^6$ is an organic group;
$R^9$ is H or an alkyl group;
$R^{10}$ is H or an alkyl group; and
p1 is an integer of 1 to 10,

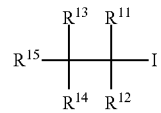
(2)

wherein
$R^{11}$ is H, F, Cl, CN, $CH_3$, $CF_3$, or $O(CF_2)_{p2}F$;
$R^{12}$ is F, Cl, CN, $-COOR^{16}$, $-PO(OR^{16})_2$, or an aryl group;
$R^{13}$ is H or F;
$R^{14}$ is H or F;
$R^{15}$ is an organic group;
$R^{16}$ is each independently H or an alkyl group; and
$p^2$ is an integer of 1 to 10,

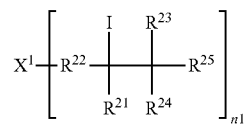
(3)

wherein
$X^1$ is an n1-valent group;
$R^{21}$ is H, F, Cl, $CH_3$, $CF_3$, or $O(CF_2)_{p3}F$;
$R^{22}$ is $-R^{26}-OCO-$, wherein $R^{26}$ is bonded to $X^1$;
$R^{23}$ is H or F;
$R^{24}$ is H, F, an aryl group, $-COOR^{30}$, or an alkyl group optionally substituted with fluorine;
$R^{25}$ is H, F, an aryl group, $-COOR^{30}$, or an alkyl group optionally substituted with fluorine;
$R^{26}$ is a single bond or an alkylene group optionally substituted with fluorine;
$R^{30}$ is H or an alkyl group;
$p^3$ is an integer of 1 to 10; and
n1 is an integer of 1 to 10, and

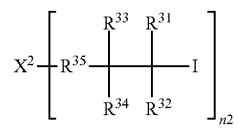
(4)

wherein
$X^2$ is an n2-valent group;
$R^{31}$ is H, F, Cl, CN, $CH_3$, $CF_3$, or $O(CF_2)_{p4}F$;
$R^{32}$ is F, Cl, CN, $-COOR^{36}$, $-PO(OR^{36})_2$, or an aryl group;
$R^{33}$ is H or a halogen atom;
$R^{34}$ is H or F;
$R^{35}$ is a single bond or an alkylene group optionally substituted with a halogen atom;
$R^{36}$ is H or an alkyl group;
p4 is an integer of 1 to 10; and
n2 is an integer of 1 to 10.

[2] The compound according to the above-described [1], which is represented by formula (1), wherein $R^2$ is —COOR$^6$;
$R^6$ is —R$^7$—R$^8$;
$R^7$ is an alkylene group optionally substituted with fluorine or a (poly)alkyleneoxy group;
$R^8$ is an alkyl group, —OH, —CH=CH$_2$, —OCH=CH$_2$, —OCO—CR$^{41}$=CH$_2$, —OCOCR$^{42}{}_2$R$^{43}$, or —SiR$^{44}{}_3$;
$R^{41}$ is H or an alkyl group;
$R^{42}$, each independently at each occurrence, is H or an alkyl group;
$R^{43}$, each independently at each occurrence, is a halogen atom; and
$R^{44}$, each independently at each occurrence, is an alkoxy group.

[3] The compound according to the above-described [1], which is represented by formula (2),
wherein $R^{15}$ is —R$^{17}$—O—CR$^{18}$=CR$^{18}{}_2$, —R$^{17}$—CR$^{18}$=CR$^{18}{}_2$, —R$^{19}$—CF$_2$I, or —R$^{20}$—O—R$^{20}$—SO$_2$F;
$R^{17}$ is each independently an alkylene group optionally substituted with fluorine;
$R^{18}$ is each independently a hydrogen atom or a halogen atom;
$R^{19}$ is a single bond or an alkylene group optionally substituted with fluorine; and
$R^{20}$ is each independently an alkylene group optionally substituted with fluorine.

[4] The compound according to the above-described [1], which is represented by formula (3),
wherein X$^1$ is an n1-valent siloxane group; and
the siloxane group is represented by the following formula:

—(SiR$^{27}{}_2$—O)$_q$—SiR$^{27}{}_2$—,

—SiR$^{28}{}_r$R$^{29}{}_{3-r}$, or (R$^a$SiO$_{1.5}$)$_t$ wherein
$R^{27}$, each independently at each occurrence, is a hydrogen atom or an alkyl group;
$R^{28}$, each independently at each occurrence, is —O—(SiR$^{27}{}_2$—O)$_s$—SiR$^{27}{}_3$—;
$R^{29}$ is a single bond;
$R^a$, each independently at each occurrence, is R$^b$ or R$^c$, provided that
at least one R$^a$ is R$^b$,
R$^b$ is a single bond, and
R$^c$ is a hydrogen atom or alkyl;
q is an integer of 1 to 20;
r is an integer of 1 to 3;
s is an integer of 0 to 20; and
t is any integer.

[5] The compound according to the above-described [1], which is represented by formula (3), wherein X$^1$ is a linear or branched n1-valent hydrocarbon group or an n1-valent aromatic group.

[6] The compound according to the above-described [1], which is represented by formula (4), wherein X$^2$ is a linear or branched n2-valent hydrocarbon group optionally substituted with fluorine.

[7] A compound represented by any of the following formulae (1A) to (4A):

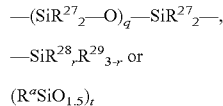

(1A)

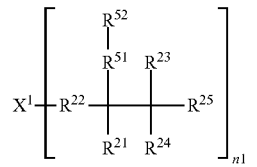

(2A)

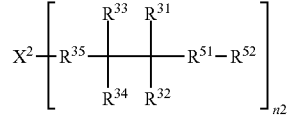

(3A)

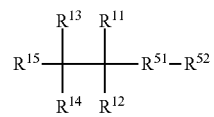

(4A)

wherein
$R^1$, $R^2$, $R^3$, $R^4$, $R^5$, $R^{11}$, $R^{12}$, $R^{13}$, $R^{14}$, $R^{15}$, X$^1$, n1, $R^{21}$, $R^{22}$, $R^{23}$, $R^{24}$, $R^{25}$, X$^2$, n2, $R^{31}$, $R^{32}$, $R^{33}$, $R^{34}$, and $R^{35}$ are as defined for the above [1];
$R^{51}$ is a polymer chain; and
$R^{52}$ is an iodine atom or a hydrogen atom.

[8] An inorganic particle comprising a compound containing I—CR$^x{}_2$—COO—, wherein R$^x$ is an optional substituent, on a surface thereof.

[9] The inorganic particle according to the above-described [8], which is a particle containing SiO$_2$ as a main component and having a compound represented by the following formula (5) on a surface thereof:

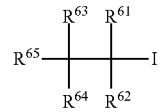

(5)

wherein
$R^{61}$ is H, F, Cl, CH$_3$, CF$_3$, or O(CF$_2$)$_{p5}$F;
$R^{62}$ is —COOR$^{66}$;
$R^{63}$ is H or F;
$R^{64}$ is H or F;
$R^{65}$ is H, F, or an alkyl group optionally substituted with fluorine;
$R^{66}$ is a single bond or —R$^{67}$—R$^{68}$;
$R^{67}$ is an alkylene group optionally substituted with fluorine or a (poly)alkyleneoxy group;
$R^{68}$ is a single bond, —O—, or —SiR$^{69}{}_u$R$^{70}{}_{3-u}$;
$R^{69}$ is a single bond;
$R^{70}$ is each independently a hydrogen atom, an alkyl group, or an alkoxy group;
u is an integer of 1 to 3; and
p5 is an integer of 1 to 10.

[10] A polymerization initiator comprising the compound according to any one of the above-described [1] to [6].

Effect of the Invention

According to the present disclosure, it is possible to provide an iodine-containing compound that can be used as a polymerization initiator species for living radical polymerization.

Embodiments to Carry Out the Invention

The present disclosure provides an iodine-containing compound represented by any of the following formulae (1) to (4), which can be used as a polymerization initiator species for living radical polymerization.

Hereinafter, an iodine-containing compound of the present disclosure will be described. The iodine-containing compound of the present disclosure is schematically characterized by having an electron-withdrawing group or an aromatic group at a carbon atom to which iodine is bonded.

Compound represented by formula (1):

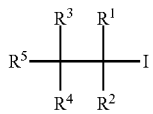

(1)

The compound represented by the above-described formula (1) is characterized by further having another functional site as $R^2$ in addition to iodine serving as a polymerization initiation point of living radical polymerization.

In the above-described formula (1), $R^1$ is H, F, Cl, $CH_3$, $CF_3$, or $O(CF_2)_{p1}F$.

The above-described p1 is an integer of 1 to 10, preferably an integer of 1 to 6, and more preferably an integer of 1 to 3.

$R^1$ is preferably H, F, $CH_3$, or $CF_3$, more preferably H or $CH_3$, and further preferably H.

In the above-described formula (1), $R^2$ is —$COOR^6$, —$PO(OR^6)_2$, —$SO_3$—$R^6$, —$SO_2$—$R^6$, —$SO$—$R^6$, -phenylen-$R^6$, or —$CONR^{10}_2$. $R^2$ is preferably —$COOR^6$ or —$PO(OR^6)_2$, and more preferably —$COOR^6$.

The above-described $R^6$ is an organic group.

The "organic group", as used herein, means a group containing carbon. Typical examples of such an organic group include linear, branched or cyclic, saturated or unsaturated, optionally substituted hydrocarbon groups, and groups having one or more of N, O, S, Si, amide, sulfonyl, siloxane, carbonyl, carbonyloxy and the like at the end of the skeleton or in the molecular chain thereof.

In one embodiment, $R^6$ is —$R^7$—$R^8$.

The above-described $R^7$ is an alkylene group or a (poly)alkyleneoxy group, which are optionally substituted with fluorine.

In one embodiment, the alkylene group optionally substituted with fluorine is a perfluoroalkylene group.

In another embodiment, the alkylene group optionally substituted with fluorine is an unsubstituted alkylene group.

In the above-described $R^7$, the "alkylene group" is an alkylene group having 10 or less carbon atoms, and may be an alkylene group having preferably 1 to 6 carbon atoms, and more preferably 2 to 6 carbon atoms. The alkylene group may be linear or branched, but it is preferably linear.

The above-described (poly)alkyleneoxy group includes a group in which the number of repetitions of the alkyleneoxy chain is 1, that is, an alkyleneoxy group and a group in which the number of repetitions of the alkyleneoxy chain is 2 or more, that is, a polyalkyleneoxy group.

The number of repetitions of the above-described (poly)alkyleneoxy group may be preferably 2 to 20, more preferably 2 to 10, and further preferably 2 to 6.

In the above-described $R^7$, the "alkylene" in the "(poly)alkyleneoxy group" is an alkylene group having 10 or less carbon atoms, and may be an alkylene group having preferably 1 to 6 carbon atoms, and more preferably 1 to 3 carbon atoms. The alkylene group may be linear or branched, but it is preferably linear.

In one embodiment, $R^8$ is an alkyl group, —OH, —$CH=CH_2$, —$OCH=CH_2$, —$OCO$—$CR^{41}=CH_2$, —$OCOCR^{42}_2R^{43}$, or —$SiR^{44}_3$.

The above-described $R^{41}$ is H or an alkyl group. The alkyl group is an alkyl group having 10 or less carbon atoms, and may be an alkyl group having preferably 1 to 6 carbon atoms, more preferably 1 to 3 carbon atoms, and further preferably a methyl group. Such an alkyl group may be linear or branched, but it is preferably linear.

In one embodiment, $R^{41}$ is H or a methyl group.

The above-described $R^{42}$, each independently at each occurrence, is H or an alkyl group. The alkyl group is an alkyl group having 10 or less carbon atoms, and may be an alkyl group having preferably 1 to 6 carbon atoms, more preferably 1 to 3 carbon atoms, and further preferably a methyl group. Such an alkyl group may be linear or branched, but it is preferably linear.

The above-described $R^{43}$, each independently at each occurrence, is a halogen atom.

The halogen atom in the above-described $R^{43}$ is fluorine, chlorine, bromine or iodine, and preferably bromine.

$R^{44}$, each independently at each occurrence, is an alkoxy group. The "alkoxy group" is an alkoxy group having 10 or less carbon atoms, and may be an alkoxy group having preferably 1 to 6 carbon atoms, and more preferably 1 to 3 carbon atoms, and further preferably a methoxy group. The alkyl group may be linear or branched, but it is preferably linear.

In one embodiment, $R^{44}$ is a methoxy group or an ethoxy group.

In one embodiment, $R^8$ is a group represented by —$SiR^{8'}_3$:
wherein
$R^{8'}$ is each independently H, an alkyl group having 1 to 3 carbon atoms, or —O—$(SiR^{8a}R^{8b}$—O$)_{n8}$—$SiR^{8c}_3$;
$R^{8a}$ and $R^{8b}$, each independently at each occurrence, are a hydrogen atom or an alkyl group having 1 to 3 carbon atoms, preferably an alkyl group having 1 to 3 carbon atoms, and more preferably a methyl group;
$R^{8c}$, each independently at each occurrence, is an alkyl group having 1 to 3 carbon atoms, and preferably a methyl group; and
n8 is an integer of 1 to 100.

The above-described $R^{10}$ is H or an alkyl group, preferably H, a methyl group, or an ethyl group.

In the above-described formula (1), $R^3$ is H or F.

In the above-described formula (1), $R^4$ is H, F, an aryl group, —$COOR^9$, or an alkyl group optionally substituted with fluorine.

In the above-described formula (1), $R^5$ is H, F, an aryl group, —$COOR^9$, or an alkyl group optionally substituted with fluorine.

The alkyl group in the above-described $R^4$ and $R^5$ is an alkyl group having 10 or less carbon atoms, and may be an alkyl group having preferably 1 to 6 carbon atoms, more preferably 1 to 3 carbon atoms, and further preferably a methyl group. The alkyl group may be linear or branched, but it is preferably linear.

The aryl group in the above-described $R^4$ and $R^5$ is an aryl group having 6 to 22 carbon atoms, and may be preferably an aryl group having 6 to 16 carbon atoms, and further preferably a phenyl group.

The above-described $R^9$ is H or an alkyl group. The alkyl group may be preferably an alkyl group having 1 to 6 carbon atoms, more preferably an alkyl group having 1 to 3 carbon atoms, and further preferably a methyl group. The alkyl group may be linear or branched, but it is preferably linear.

In one embodiment, a compound represented by the above-described formula (1) is a compound wherein
$R^1$ is H, F, Cl, $CH_3$, $CF_3$, or $O(CF_2)_{p1}F$, and preferably H or $CH_3$;
$R^2$ is $-COOR^6$;
$R^3$ is H or F;
$R^4$ is H or F;
$R^5$ is H, F, or an alkyl group having 1 to 6 carbon atoms optionally substituted with fluorine, and preferably a perfluoroalkyl group having 1 to 6 carbon atoms;
$R^6$ is $-R^7-R^8$;
$R^7$ is an alkylene group having 1 to 6 carbon atoms or a (poly) $C_{1-6}$ alkyleneoxy group, which are optionally substituted with fluorine, and preferably an alkylene group having 1 to 6 carbon atoms;
$R^8$ is $-CH=CH_2$, $-OCH=CH_2$, or $-OCO-CR^{41}=CH_2$;
$R^{41}$ is H or a methyl group; and
p1 is an integer of 1 to 10.

Since the above-described compound has iodine, it functions as a polymerization initiator for living radical polymerization. Furthermore, since the above-described compound has an ethylenic double bond, it also functions as a monomer.

In one embodiment, a compound represented by the above-described formula (1) is a compound wherein
$R^1$ is H, F, Cl, $CH_3$, $CF_3$, or $O(CF_2)_{p1}F$, and preferably H or $CH_3$;
$R^2$ is $-COOR^6$;
$R^3$ is H or F;
$R^4$ is H or F;
$R^5$ is H, F, or an alkyl group having 1 to 6 carbon atoms optionally substituted with fluorine, and preferably a perfluoroalkyl group having 1 to 6 carbon atoms;
$R^6$ is $-R^7-R^8$;
$R^7$ is an alkylene group having 1 to 6 carbon atoms or a poly $C_{1-6}$ alkyleneoxy group;
when $R^7$ is an alkylene group having 1 to 6 carbon atoms, $R^8$ is $-OH$, and when $R^7$ is a poly $C_{1-6}$ alkyleneoxy group, $R^8$ is an alkyl group having 1 to 3 carbon atoms, and preferably a methyl group; and
p1 is an integer of 1 to 10.

Since the above-described compound has iodine, it functions as a polymerization initiator for living radical polymerization. Furthermore, since the above-described compound has a hydroxyl group or a polyalkyleneoxy group at the end, it also functions as a hydrophilizing agent.

In one embodiment, a compound represented by the above-described formula (1) is a compound wherein
$R^1$ is H, F, Cl, $CH_3$, $CF_3$, or $O(CF_2)_{p1}F$, and preferably H or $CH_3$;
$R^2$ is $-COOR^6$;
$R^3$ is H or F;
$R^4$ is H or F;
$R^5$ is $-COOR^9$;
$R^6$ is $-R^7-R^8$;
$R^7$ is an alkylene group having 1 to 6 carbon atoms or a poly $C_{1-6}$ alkyleneoxy group, and preferably an alkylene group having 1 to 6 carbon atoms;
$R^8$ is $-SiR^{44}_3$;
$R^9$ is a hydrogen atom or an alkyl group having 1 to 3 carbon atoms; and
$R^{44}$, each independently at each occurrence, is a methoxy group or an ethoxy group.

Since the above-described compound has iodine, it functions as a polymerization initiator for living radical polymerization. Furthermore, since the above-described compound has a Si atom having a hydrolyzable group at the end, it also functions as a silane coupling agent.

In one embodiment, a compound represented by the above-described formula (1) is a compound wherein
$R^1$ is H, F, Cl, $CH_3$, $CF_3$, or $O(CF_2)_{p1}F$, and preferably H or $CH_3$;
$R^2$ is $-COOR^6$;
$R^3$ is H or F;
$R^4$ is H or F;
$R^5$ is H, F, or an alkyl group having 1 to 6 carbon atoms optionally substituted with fluorine, and preferably a perfluoroalkyl group having 1 to 6 carbon atoms;
$R^6$ is $-R^7-R^8$;
$R^7$ is an alkylene group having 1 to 6 carbon atoms or a poly $C_{1-6}$ alkyleneoxy group, and preferably an alkylene group having 1 to 6 carbon atoms;
$R^8$ is $-OCOCR^{42}_2SiR^{43}$;
$R^{42}$, each independently at each occurrence, is H or an alkyl group having 1 to 3 carbon atoms;
$R^{43}$, each independently at each occurrence, is a halogen atom, and preferably bromine; and
$p^1$ is an integer of 1 to 10.

Since the above-described compound has iodine, it functions as a polymerization initiator for living radical polymerization. Furthermore, since the above-described compound has a $-OCOC$ halogen skeleton, it also functions as an initiator for atom transfer radical polymerization.

Compound represented by formula (2):

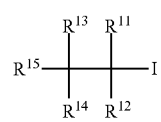

(2)

The compound represented by the above-described formula (2) is characterized by further having another functional site as $R^{15}$ in addition to iodine serving as a polymerization initiation point of living radical polymerization.

In the above-described formula (2), $R^{11}$ is H, F, Cl, $CH_3$, $CF_3$, or $O(CF_2)_{p2}F$.

The above-described p2 is an integer of 1 to 10, preferably an integer of 1 to 6, and more preferably an integer of 1 or 3.

$R^{11}$ is preferably H, F, $CH_3$, or $CF_3$, more preferably H or $CH_3$, and further preferably H.

$R^{12}$ is F, Cl, $-COOR^{16}$, $-PO(OR^{16})_2$, or an aryl group.

$R^{16}$ is each independently H or an alkyl group. The alkyl group is an alkyl group having 10 or less carbon atoms, and may be an alkyl group having preferably 1 to 6 carbon atoms, more preferably 1 to 3 carbon atoms, and further preferably a methyl group. Such an alkyl group may be linear or branched, but it is preferably linear.

The above-described aryl group is preferably a phenyl group. The phenyl group may be substituted. Examples of the substituent is not limited, but include, for example, a halogen atom, preferably a fluorine atom; and one or more groups selected from a $C_{1-6}$ alkyl group, a $C_{2-6}$ alkenyl group, a $C_{2-6}$ alkynyl group, a $C_{3-10}$ cycloalkyl group, a $C_{3-10}$ unsaturated cycloalkyl group, a 5 to 10-membered heterocyclyl group, a 5 to 10-membered unsaturated heterocyclyl group, a $C_{6-10}$ aryl group and a 5 to 10-membered heteroaryl group each optionally substituted with one or more halogen atoms.

In one embodiment, the above-described substituent is a fluorine atom.

In the above-described formula (2), $R^{13}$ is H or F.

In the above-described formula (2), $R^{14}$ is H or F.

In the above-described formula (2), $R^{15}$ is an organic group.

In one embodiment, $R^{15}$ is $-R^{17}-O-CR^{18}=CR^{18}{}_2$, $-R^{17}-CR^{18}=CR^{18}{}_2$, $-R^{19}-CF_2I$, or $-R^{20}-O-R^{20}-SO_2F$.

The above-described $R^{17}$ is each independently an alkylene group optionally substituted with fluorine.

In the above-described $R^{17}$, the "alkylene group" is an alkylene group having 10 or less carbon atoms, and may be an alkylene group having preferably 1 to 6 carbon atoms, and more preferably 2 to 6 carbon atoms. The alkylene group may be linear or branched, but it is preferably linear.

In one embodiment, $R^{17}$ is an alkylene group having 1 to 6 carbon atoms.

In another embodiment, $R^{17}$ is an alkylene group having 1 to 6 carbon atoms substituted with a fluorine atom.

The above-described $R^{18}$ is each independently a hydrogen atom or a halogen atom. The halogen atom is a fluorine atom, a chlorine atom, a bromine atom, or an iodine atom. The halogen atom is preferably a fluorine atom or a chlorine atom.

The above-described $R^{19}$ is a single bond or an alkylene group optionally substituted with a fluorine atom.

In the above-described $R^{19}$, the "alkylene group" is an alkylene group having 10 or less carbon atoms, and may be an alkylene group having preferably 1 to 6 carbon atoms, and more preferably 2 to 6 carbon atoms. The alkylene group may be linear or branched, but it is preferably linear.

In one embodiment, $R^{19}$ is an alkylene group optionally substituted with fluorine, and preferably an alkylene group substituted with fluorine.

In one embodiment, $R^{20}$ is each independently an alkylene group optionally substituted with fluorine, and preferably a perfluoroalkylene group. The "alkylene group" in the alkylene group optionally substituted with fluorine may be preferably an alkylene group having 1 to 10 carbon atoms, and more preferably an alkylene group having 2 to 4 carbon atoms.

In one embodiment, a compound represented by the above-described formula (2) is a compound wherein
$R^{11}$ is H, F, Cl, $CH_3$, $CF_3$, or $O(CF_2)_{p2}F$;
$R^{12}$ is $-COOR^{16}$;
$R^{13}$ is H or F;
$R^{14}$ is H or F;
$R^{16}$ is each independently H or an alkyl group having 1 to 3 carbon atoms;
$R^{15}$ is $-R^{17}-O-CR^{18}=CR^{18}{}_2$, $-R^{17}-CR^{18}=CR^{18}{}_2$;
$R^{17}$ is each independently an alkylene group having 1 to 6 carbon atoms optionally substituted with fluorine;
$R^{18}$ is each independently a hydrogen atom or a halogen atom, and preferably a fluorine atom; and
p2 is an integer of 1 to 10.

Since the above-described compound has iodine, it functions as a polymerization initiator for living radical polymerization. Furthermore, since the above-described compound has an ethylenic double bond, it also functions as a monomer.

In one embodiment, a compound represented by the above-described formula (2) is a compound wherein
$R^{11}$ is H, F, Cl, $CH_3$, $CF_3$, or $O(CF_2)_{p2}F$;
$R^{12}$ is $-COOR^{16}$;
$R^{13}$ is H or F;
$R^{14}$ is H or F;
$R^{16}$ is each independently H or an alkyl group having 1 to 3 carbon atoms;
$R^{15}$ is $-R^{19}-CF_2I$;
$R^{19}$ is each independently an alkylene group having 1 to 10 carbon atoms optionally substituted with fluorine; and
p2 is an integer of 1 to 10.

Since the above-described compound has iodine, it functions as a polymerization initiator for living radical polymerization. Furthermore, since the above-described compound has $-CF_2I$, it also functions as an initiator and a chain transfer agent for iodine transfer polymerization.

Compound represented by formula (3):

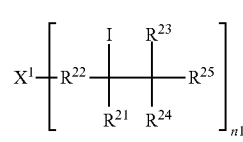

(3)

In the above-described formula, $X^1$ is an n1-valent group.

The above-described n1 is an integer of 1 to 10, and may be preferably an integer of 1 to 8, and more preferably an integer of 1 or 6.

In one embodiment, $X^1$ is an n1-valent siloxane group.

The above-described $X^1$ is preferably a siloxane group represented by any of the following formulae (i) to (iii):

$$-(SiR^{27}{}_2-O)_q-SiR^{27}{}_2- \quad \text{(i)}$$

$$-SiR^{28}{}_rR^{29}{}_{3-r} \quad \text{(ii)}$$

$$(R^aSiO_{1.5})_t \quad \text{(iii)}$$

wherein
$R^{27}$, each independently at each occurrence, are a hydrogen atom or an alkyl group (preferably alkyl group having 1 to 3 carbon atoms, and more preferably a methyl group);
$R^{28}$, each independently at each occurrence, is $-O-(SiR^{27}{}_2-O)_s-SiR^{27}{}_3-$;
$R^{29}$ is a single bond (that is, a bond);
$R^a$, each independently at each occurrence, is $R^b$ or $R^c$, provided that
at least one $R^a$ is $R^b$,
$R^b$ is a single bond, and
$R^c$ is a hydrogen atom or an alkyl (preferably alkyl group having 1 to 6 carbon atoms, and more preferably 1 to 4 carbon atoms);
q is an integer of 1 to 20;
r is an integer of 1 to 3, and preferably an integer of 1 to 2;

s is an integer of 0 to 20; and t is any integer such as 6 to 16, preferably 6 to 14, and particularly preferably 8.

The siloxane group represented by the above-described formula (i) is a divalent siloxane group.

In a preferable embodiment, in formula (i), $R^{27}$ is a methyl group, and q is an integer of 1 to 20.

The siloxane group represented by the above-described formula (ii) is a mono- to trivalent siloxane group.

In a preferable embodiment, in formula (ii), $R^{28}$, each independently at each occurrence, is —O—$(SiR^{27}_2$—O$)_s$—$SiR^{27}_3$—, and $R^{27}$ is a methyl group.

The siloxane group represented by the above-described formula (iii) is so-called silsesquioxane.

The siloxane group represented by the above-described formula (iii) may be any of a random, cage-type, or ladder-type silsesquioxane, preferably a cage-like or ladder-type silsesquioxane, and more preferably a cage-type silsesquioxane.

In a preferable embodiment, the siloxane group represented by the above-described formula (iii) is a cage-type silsesquioxane compound wherein t is 8.

In one embodiment, $X^1$ is a linear or branched n1-valent hydrocarbon group or an n1-valent aromatic group.

Specific examples of the above-described linear or branched n1-valent hydrocarbon group include, for example, the following groups:

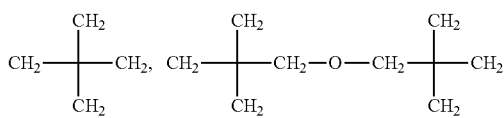

Specific examples of the above-described n1-valent aromatic group include, for example, the following groups:

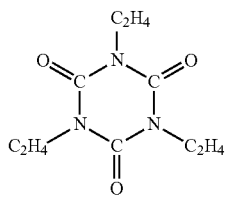

In the above-described formula (3), $R^{21}$ is H, F, Cl, $CH_3$, $CF_3$, or $O(CF_2)_{p1}F$.

The above-described p3 is an integer of 1 to 10, preferably an integer of 1 to 6, and more preferably an integer of 1 or 3.

$R^{21}$ is preferably H, F, $CH_3$, or $CF_3$, more preferably H or $CH_3$, and further preferably H.

In the above-described formula (3), $R^{22}$ is —$R^{26}$—OCO—, where $R^{26}$ is bonded to $X^1$.

The above-described $R^{26}$ is a single bond or an alkylene group optionally substituted with fluorine.

In the above-described $R^{26}$, the "alkylene group" is an alkylene group having 10 or less carbon atoms, and may be an alkylene group having preferably 1 to 6 carbon atoms, and more preferably 2 to 6 carbon atoms. The alkylene group may be linear or branched, but it is preferably linear.

In one embodiment, $R^{26}$ is an unsubstituted alkylene group having 1 to 6 carbon atoms, and more preferably 2 to 6 carbon atoms.

In the above-described formula (3), $R^{23}$ is H or F.

In the above-described formula (3), $R^{24}$ is H or F.

In the above-described formula (3), $R^{25}$ is H, F, or an alkyl group optionally substituted with fluorine. The alkyl group is an alkyl group having 10 or less carbon atoms, and may be an alkyl group having preferably 1 to 6 carbon atoms, more preferably 1 to 3 carbon atoms, and further preferably a methyl group. The alkyl group may be linear or branched, but it is preferably linear.

In a preferable embodiment, the above-described alkyl group optionally substituted with fluorine is a perfluoroalkyl group.

In one embodiment, a compound represented by the above-described formula (3) is a compound wherein $X^1$ is a siloxane group represented by the following formula:

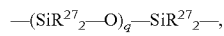

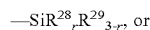

wherein
$R^{27}$, each independently at each occurrence, is a hydrogen atom or an alkyl group;
$R^{28}$, each independently at each occurrence, is —O—$(SiR^{27}_2$—O$)_s$—$SiR^{27}_3$—;
$R^{29}$ is a single bond;
$R^a$, each independently at each occurrence, is $R^b$ or $R^c$, provided that
at least one $R^a$ is $R^b$,
$R^b$ is a single bond, and
$R^c$ is a hydrogen atom or alkyl;
q is an integer of 1 to 20;
r is an integer of 1 to 3;
s is an integer of 0 to 20; and
t is any integer such as 6 to 16, preferably 6 to 14, and particularly preferably 8;
$R^{21}$ is H, F, Cl, $CH_3$, $CF_3$, or $O(CF_2)_{p3}F$;
$R^{22}$ is —$R^{26}$—OCO— wherein $R^{26}$ is bonded to $X^1$;
$R^{23}$ is H or F;
$R^{24}$ is H or F;
$R^{25}$ is H, F, or an alkyl group having 1 to 6 carbon atoms optionally substituted with fluorine, and preferably a perfluoroalkyl group having 1 to 6 carbon atoms;
$R^{26}$ is a single bond or an alkylene group having 1 to 3 carbon atoms, and preferably an alkylene group having 1 to 3 carbon atoms;
p3 is an integer of 1 to 10; and
n1 is an integer of 1 to 10.

Since the above-described compound has iodine, it functions as a polymerization initiator for living radical polymerization. Furthermore, since the above-described compound has a siloxane skeleton, it also functions as various additives.

In one embodiment, a compound represented by the above-described formula (3) is a compound wherein
$X^1$ is a group represented by the following formula:

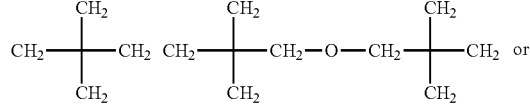

-continued

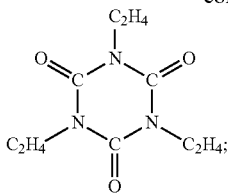

$R^{21}$ is H, F, Cl, $CH_3$, $CF_3$, or $O(CF_2)_{p3}F$;
$R^{22}$ is $-R^{26}-OCO-$, where $R^{26}$ is bonded to $X^1$;
$R^{23}$ is H or F;
$R^{24}$ is H or F;
$R^{25}$ is H, F, or an alkyl group having 1 to 6 carbon atoms optionally substituted with fluorine, and preferably a perfluoroalkyl group having 1 to 6 carbon atoms;
$R^{26}$ is a single bond or an alkylene group having 1 to 3 carbon atoms, and preferably an alkylene group having 1 to 3 carbon atoms;
p3 is an integer of 1 to 10; and
n1 is an integer of 1 to 10.

Since the above-described compound has iodine, it functions as a polymerization initiator for living radical polymerization. Since the above-described compound may have a plurality of iodine atoms, it can be used for the synthesis of a polyfunctional polymer, a star polymer and the like.

Compound represented by formula (4):

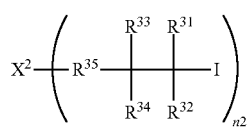

In the above-described formula, $X^2$ is an n2-valent group.

The above-described n2 is an integer of 1 to 10, and may be preferably an integer of 1 to 8, and more preferably an integer of 1 or 6.

In a preferable embodiment, $X^2$ is a linear or branched n2-valent hydrocarbon group optionally substituted with fluorine.

Examples of the above-described linear or branched n2-valent hydrocarbon group optionally substituted with fluorine include, for example, an alkylene group having 1 to 10 carbon atoms optionally substituted with a fluorine atom, and the like.

In another preferable embodiment, $X^2$ is an n2-valent siloxane group.

The above-described $X^2$ is preferably a siloxane group represented by any of the following formulae (i) to (iii):

The above-described siloxane group represented by any of formulae (i) to (iii) is the same as those described for $X^1$.

In the above-described formula (4), $R^{31}$ is H, F, Cl, $CH_3$, $CF_3$, or $O(CF_2)_{p4}F$.

The above-described p4 is an integer of 1 to 10, preferably an integer of 1 to 6, and more preferably an integer of 1 or 3.

$R^{31}$ is preferably H, F, $CH_3$, or $CF_3$, more preferably H or $CH_3$, and further preferably H.

In the above-described formula (4), $R^{32}$ is F, Cl, $-COOR^{36}$, $-PO(OR^{36})_2$, or an aryl group.

$R^{36}$ is each independently H or an alkyl group. The alkyl group is an alkyl group having 10 or less carbon atoms, and may be an alkyl group having preferably 1 to 6 carbon atoms, more preferably 1 to 3 carbon atoms, and further preferably a methyl group. The alkyl group may be linear or branched, but it is preferably linear.

The above-described aryl group is preferably a phenyl group. The phenyl group may be substituted. Examples of the substituent is not limited, but include, for example, a halogen atom, preferably a fluorine atom; and one or more groups selected from a $C_{1-6}$ alkyl group, a $C_{2-6}$ alkenyl group, a $C_{2-6}$ alkynyl group, a $C_{3-10}$ cycloalkyl group, a $C_{3-10}$ unsaturated cycloalkyl group, a 5 to 10-membered heterocyclyl group, a 5 to 10-membered unsaturated heterocyclyl group, a $C_{6-10}$ aryl group and a 5 to 10-membered heteroaryl group each optionally substituted with one or more halogen atoms.

In the above-described formula (4), $R^{33}$ is H or a halogen atom.

The above-described halogen atom is a fluorine atom, a chlorine atom, a bromine atom, or an iodine atom. In one embodiment, the halogen atom is a fluorine atom. In another embodiment, the halogen atom is a bromine atom or an iodine atom, and preferably an iodine atom.

In the above-described formula (4), $R^{34}$ is H or F.

In the above-described formula (4), $R^{35}$ is a single bond or an alkylene group optionally substituted with a halogen atom.

The above-described halogen atom is one or more atoms selected from a fluorine atom, a chlorine atom, a bromine atom, and an iodine atom.

In the above-described $R^{35}$, the "alkylene group" is an alkylene group having 10 or less carbon atoms, and may be an alkylene group having preferably 1 to 6 carbon atoms, and more preferably 2 to 6 carbon atoms. The alkylene group may be linear or branched, but it is preferably linear.

In one embodiment, $R^{35}$ is an unsubstituted alkylene group having 1 to 6 carbon atoms, and more preferably 2 to 6 carbon atoms.

In another embodiment, $R^{35}$ is $-CHZ_1-R^{39}-$.

$Z_1$ is a bromine atom or an iodine atom, and preferably an iodine atom.

$R^{39}$ is an alkylene group having 1 to 10 carbon atoms optionally substituted with a fluorine atom, and preferably 1 to 6 carbon atoms. $R^{39}$ is preferably $-CH_2-R^{39a}-$.

$R^{39a}$ is a perfluoroalkylene group having 1 to 6 carbon atoms.

In one preferable embodiment, $R^{35}$ is $-CHI-CH_2-R^{39a}-$.

In one embodiment, a compound represented by the above-described formula (4) is a compound wherein
$X^2$ is an alkylene group having 1 to 10 carbon atoms optionally substituted with a fluorine atom, and preferably a perfluoroalkylene group having 1 to 6 carbon atoms;
$R^{31}$ is H, F, Cl, $CH_3$, $CF_3$, or $O(CF_2)_{p4}F$;
$R^{32}$ is F, Cl, $-COOR^{36}$, $-PO(OR^{36})_2$, or an aryl group, and preferably $-COOR^{36}$;
$R^{33}$ is H or F;
$R^{34}$ is H or F;
$R^{35}$ is a single bond or an alkylene group having 1 to 6 carbon atoms optionally substituted with fluorine, and preferably an alkylene group having 1 to 6 carbon atoms;
$R^{36}$ is H or an alkyl group having 1 to 3 carbon atoms;

$p^4$ is an integer of 1 to 10; and n2 is 2.

Since the above-described compound has iodine, it functions as a polymerization initiator for living radical polymerization. Since the above-described compound may have a plurality of iodine atoms, it can be used for the synthesis of a polyfunctional polymer, a star polymer and the like.

The above-described compound represented by any of formulae (1) to (4) can be obtained by the reaction between a compound having a double bond and an iodide. For example, the compound represented by formula (1) can be obtained by the reaction between $CR^1R^2$=$CR^3R^4$ and $R^5$—I. The compound represented by formula (2) can be obtained by the reaction between $CR^{11}R^{12}$=$CR^{13}R^{14}$ and $R^{15}$—I. The compound represented by formula (3) can be obtained by the reaction between $X^1$—$(R^{22}$—$CR^{21}$=$CR^{23}R^{24})_{n1}$ and $R^{25}$—I. The compound represented by formula (4) can be obtained by the reaction between $CR^{31}R^{32}$=$CR^{33}R^{34}$ and $X^2$—$(R^{35}$—$I)_{n2}$.

The above-described compound represented by any of formulae (1) to (4) can be used as an initiator for living radical polymerization. That is, the compound represented by any of formulae (1) to (4) reacts with a monomer to form a polymer.

As such, the present disclosure also discloses a polymer obtained by polymerizing a monomer to the compound represented by any of formulae (1) to (4) of the present disclosure.

In one embodiment, the above-described monomer is a monomer having at least one fluorine atom (hereinafter, may also be referred to as a "fluorine-containing monomer").

In one embodiment, the above-described fluorine-containing monomer may be a compound having a perfluoropolyether group or a perfluoroalkyl group, and a polymerizable group A.

The above-described fluorine-containing monomer may have two or more perfluoropolyether groups or perfluoroalkyl groups, and polymerizable group A.

The above-described perfluoroalkyl group is a group represented by $C_jF_{2j+1}$, wherein j is an integer of 1 to 30, preferably an integer of 3 to 20 such as an integer of 5 to 10. The perfluoroalkyl group may be linear or branched, but it is preferably linear.

In one embodiment, the above-described perfluoroalkyl group is a linear perfluoroalkyl group having 1 to 10 carbon atoms. In particular, the above-described perfluoroalkyl group is represented by F—$(CF_2)_n$, wherein n is an integer of 1 to 10, and more preferably, n is an integer of 4 to 8 such as 6.

The above-described perfluoropolyether group (hereinafter, may also be referred to as "PFPE") is a group represented by the following formula:

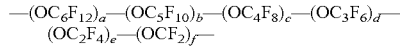

wherein a, b, c, d, e and f are each independently an integer of 0 or more and 200 or less, and the sum of a, b, c, d, e and f is at least 1. Preferably, a, b, c, d, e and f are each independently an integer of 0 or more and 100 or less. The sum of a, b, c, d, e and f is preferably 5 or more and more preferably 10 or more. The sum of a, b, c, d, e and f is preferably 200 or less and more preferably 100 or less. For example, it is 10 or more and 200 or less, and more specifically 10 or more and 100 or less. In addition, the occurrence order of each repeating unit, which is shown in parenthesis subscripted with a, b, c, d, e or f, is not limited in the formula.

These repeating units may be linear or branched, but they are preferably linear. For example, —$(OC_6F_{12})$— may be —$(OCF_2CF_2CF_2CF_2CF_2CF_2)$—, —$(OCF(CF_3)CF_2CF_2CF_2CF_2)$—, —$(OCF_2CF(CF_3)CF_2CF_2CF_2)$—, —$(OCF_2CF_2CF(CF_3)CF_2CF_2)$—, —$(OCF_2CF_2CF_2CF(CF_3)CF_2)$—, —$(OCF_2CF_2CF_2CF_2CF(CF_3))$— or the like, but it is preferably —$(OCF_2CF_2CF_2CF_2CF_2CF_2)$—. —$(OC_5F_{10})$— may be —$(OCF_2CF_2CF_2CF_2CF_2)$—, —$(OCF(CF_3)CF_2CF_2CF_2)$—, —$(OCF_2CF(CF_3)CF_2CF_2)$—, —$(OCF_2CF_2CF(CF_3)CF_2)$—, —$(OCF_2CF_2CF_2CF(CF_3))$— or the like, but it is preferably —$(OCF_2CF_2CF_2CF_2CF_2)$—. —$(OC_4F_8)$— may be any of —$(OCF_2CF_2CF_2CF_2)$—, —$(OCF(CF_3)CF_2CF_2)$—, —$(OCF_2CF(CF_3)CF_2)$—, —$(OCF_2CF_2CF(CF_3))$—, —$(OC(CF_3)_2CF_2)$—, —$(OCF_2C(CF_3)_2)$—, —$(OCF(CF_3)CF(CF_3))$—, —$(OCF(C_2F_5)CF_2)$— and —$(OCF_2CF(C_2F))$—, but it is preferably —$(OCF_2CF_2CF_2CF_2)$—. —$(OC_3F_6)$— may be any of —$(OCF_2CF_2CF_2)$—, —$(OCF(CF_3)CF_2)$— and —$(OCF_2CF(CF_3))$—, but it is preferably —$(OCF_2CF_2CF_2)$—. In addition, —$(OC_2F_4)$— may be any of —$(OCF_2CF_2)$— and —$(OCF(CF_3))$—, but it is preferably —$(OCF_2CF_2)$—.

In one embodiment, the above-described PFPE is —$(OC_3F_6)_d$—, wherein d is an integer of 1 or more and 200 or less, preferably 5 or more and 200 or less, and more preferably 10 or more and 200 or less. Preferably, PFPE is —$(OCF_2CF_2CF_2)_d$—, wherein d is an integer of 1 or more and 200 or less, preferably 5 or more and 200 or less, and more preferably 10 or more and 200 or less, or —$(OCF(CF_3)CF_2)_d$—, wherein d is an integer of 1 or more and 200 or less, preferably 5 or more and 200 or less, and more preferably 10 or more and 200 or less. More preferably, PFPE is —$(OCF_2CF_2CF_2)_d$—, wherein d is an integer of 1 or more and 200 or less, preferably 5 or more and 200 or less, and more preferably 10 or more and 200 or less.

In another embodiment, PFPE is —$(OC_4F)_c$—$(OC_3F_6)_d$—$(OC_2F_4)_e$—$(OCF_2)_f$—, wherein: c and d are each independently an integer of 0 or more and 30 or less; e and f are each independently an integer of 1 or more and 200 or less, preferably 5 or more and 200 or less, and more preferably 10 or more and 200 or less; the sum of c, d, e and 0f is preferably an integer of 10 or more and 200 or less; and the occurrence order of each repeating unit, which is shown in parenthesis subscripted with c, d, e or f, is not limited in the formula. Preferably, PFPE is —$(OCF_2CF_2CF_2CF_2)_c$—$(OCF_2CF_2CF_2)_d$—$(OCF_2CF_2)_e$—$(OCF_2)_f$—. In one embodiment, PFPE may be —$(OC_2F_4)_e$—$(OCF_2)_f$—, wherein e and f are each independently an integer of 1 or more and 200 or less, preferably 5 or more and 200 or less, and more preferably 10 or more and 200 or less, and the occurrence order of each repeating unit, which is shown in parenthesis subscripted with e or f, is not limited in the formula.

In still another embodiment, PFPE is a group represented by —$(R^{55}$—$R^{56})_k$—, wherein $R^{55}$ is $OCF_2$ or $OC_2F_4$, and preferably $OC_2F_4$; and $R^{56}$ is a group selected from $OC_2F_4$, $OC_3F_6$, $OC_4F_8$, $OC_5F_{10}$, and $OC_6F_{12}$, or alternatively a combination of two or three groups independently selected from these groups. Preferably, $R^{56}$ is a group selected from $OC_2F_4$, $OC_3F_6$, and $OC_4F_8$, or alternatively a combination of two or three groups independently selected from these groups. Examples of the combination of two or three groups independently selected from $OC_2F_4$, $OC_3F_6$ and $OC_4F_8$ are not limited, but include, for example, —$OC_2F_4OC_3F_6$—, —$OC_2F_4OC_4F_8$—, —$OC_3F_6OC_2F_4$—, —$OC_3F_6OC_3F_6$—, —$OC_3F_6OC_4F_8$—, —$OC_4F_8OC_4F_8$—, —$OC_4F_8OC_3F_6$—, —$OC_4F_8OC_2F_4$—, —$OC_2F_4OC_2F_4OC_3F_6$—, —OC$_2$F$_4$OC$_2$F$_4$OC$_4$F$_8$—, —OC$_2$F$_4$OC$_3$F$_6$OC$_2$F$_4$—, —OC$_2$F$_4$OC$_3$F$_6$OC$_3$F$_6$—, —OC$_2$F$_4$OC$_4$F$_8$OC$_2$F$_4$—, —OC$_3$F$_6$OC$_2$F$_4$OC$_2$F$_4$—, —OC$_3$F$_6$OC$_2$F$_4$OC$_3$F$_6$—, —OC$_3$F$_6$OC$_3$F$_6$OC$_2$F$_4$—, —OC$_4$F$_8$OC$_2$F$_4$OC$_2$F$_4$— and the like. The above-described k is an integer of 2 to 100, and preferably an integer of 2 to 50. In the above-described formula, OC$_2$F$_4$, OC$_3$F$_6$, OC$_4$F$_8$, OC$_5$F$_{10}$ and OC$_6$F$_{12}$ may be either linear or branched, and they are preferably linear. In this embodiment, PFPE is preferably —(OC$_2$F$_4$—OC$_3$F$_6$)$_k$— or —(OC$_2$F$_4$—OC$_4$F$_8$)$_k$—.

In one embodiment, PFPE may be a group having a ((αβ)$_i$) chain composed of two or more linking (αβ) units, wherein the (αβ) unit has one to three (α) groups composed of at least one of oxyperfluoroalkylene groups having 1 to 2 carbon atoms and one to three (β) groups composed of at least one of oxyperfluoroalkylene groups having 3 to 6 carbon atoms.

The above-described compound may have another oxyperfluoroalkylene group not belonging to the ((αβ)$_i$) chain.

The order of (α) groups and (β) groups in the (αβ) unit is not limited. For example, when two (α) groups are present, these two (α) groups may be directly bonded or may be bonded via at least one (β) group.

The above-described PFPE may have a ((αβ)$_i$) chain composed of two or more linking (αβ) units. When one end of the unit (αβ) is the (α) group and the other end is the (β) group, in the ((αβ)$_i$) chain, it is preferable that two or more (αβ) units be linked in a way such that the (α) group and the (β) group are arranged alternately between units. That is, it is preferable that adjoining (αβ) units be bonded to form a head-to-tail structure. In the (αβ) unit, the bonding order of (α) groups and (β) groups is not limited. That is, (α) groups and (3) groups may be arranged randomly, (α) groups and (3) groups may be arranged alternately, or two or more blocks composed of a plurality of groups may be linked.

Examples of the (αβ) unit include the following: (CF$_2$CF$_2$O—CF$_2$CF$_2$CF$_2$O), (CF$_2$CF$_2$O—CF$_2$CF$_2$CF$_2$CF$_2$O), (CF$_2$CF$_2$O—CF$_2$CF$_2$CF$_2$OCF$_2$CF$_2$CF$_2$O), (CF$_2$CF$_2$O—CF$_2$CF(CF$_3$)OCF$_2$CF$_2$O), (CF$_2$CF$_2$O—CF$_2$CF$_2$CF$_2$CF$_2$OCF(CF$_3$)CF$_2$O).

In particular, a preferable embodiment of the above-described PFPE is represented by the following formula

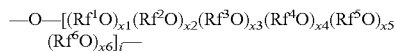

wherein the symbols in the formula are as follows:
i is an integer of 1 or more, and preferably an integer of 2 or more, the upper limit of i is preferably 45, and i is preferably 4 to 40 and particularly preferably 5 to 35;
x1 to x2 are each independently an integer of 0 to 3, and x1+x2 is an integer of 1 to 3;
x3 to x6 are each independently an integer of 0 to 3, and x3+x4+x5+x6 is an integer of 1 to 3;
Rf$^1$ is a perfluoroalkylene group having 1 carbon atom;
Rf$^2$ is a perfluoroalkylene group having 2 carbon atoms;
Rf$^3$ is a perfluoroalkylene group having 3 carbon atoms;
Rf$^4$ is a perfluoroalkylene group having 4 carbon atoms;
Rf$^5$ is a perfluoroalkylene group having 5 carbon atoms; and
Rf$^6$ is a perfluoroalkylene group having 6 carbon atoms.

Examples of the above-described polymerizable group A are not limited, but include, for example, a group having an ethylenic double bond, as well as derivatives thereof.

The polymerizable group A is preferably a group represented by the following formula:

wherein
R$^{163}$ is a single bond, —O—, —CO— or —OC(O)—;
R$^{164}$ represents a hydrogen atom, a fluorine atom, or an alkyl group having 1 to 10 carbon atoms (preferably an alkyl group having 1 to 3 carbon atoms, and more preferably a methyl group) optionally substituted with a fluorine atom, a lactam group (preferably a β-lactam, γ-lactam or δ-lactam group, and more preferably a γ-lactam group) or a phenyl group where the alkyl group, the lactam group and the phenyl group are optionally substituted with a fluorine atom, and is preferably a methyl group or a hydrogen atom; and
R$^{165}$ each independently represents a hydrogen atom or a fluorine atom, and is preferably a hydrogen atom.

In the present embodiment, a preferable polymerizable group A is a group represented by the following formula:

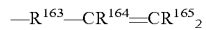

wherein
R$^{163}$ is a single bond or —OC(O)—; and
R$^{164}$ represents a hydrogen atom, a fluorine atom, or an alkyl group having 1 to 10 carbon atoms (preferably an alkyl group having 1 to 3 carbon atoms, and more preferably a methyl group), a lactam group (preferably a β-lactam, γ-lactam or δ-lactam group, and more preferably a γ-lactam group) or a phenyl group wherein the alkyl group, the lactam group and the phenyl group are optionally substituted with a fluorine atom, and is preferably a methyl group or a hydrogen atom, and it preferably represents a hydrogen atom, a fluorine atom, or an alkyl group having 1 to 10 carbon atoms (preferably an alkyl group having 1 to 3 carbon atoms, and more preferably a methyl group) or a phenyl group wherein the alkyl group and the phenyl group are optionally substituted with a fluorine atom, and is more preferably a methyl group or a hydrogen atom; and
R$^{165}$ is as defined above.

A more preferable polymerizable group A is a group represented by the following formula:

wherein R$^{164}$ and R$^{165}$ are as defined above.

A further preferable polymerizable group A is an acryloyl group or a methacryloyl group.

Examples of the fluorine-containing monomer are not limited, but include, for example, at least one compound represented by any of the following formulae (A1), (A2), (B1), and (B2):

 (A1)

 (A2)

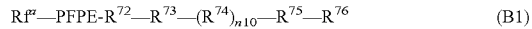 (B1)

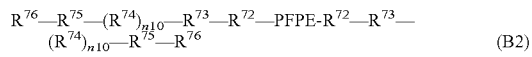 (B2)

wherein
Rf$^a$ each independently represents an alkyl group having 1 to 16 carbon atoms optionally substituted with one or more fluorine atoms;

PFPE is as defined above;

$R^{71}$ each independently represents a polymerizable group A;

X represents a divalent organic group;

$R^{72}$ is a group represented by the following formula:

$$-(Q)_{e1}-(CFZ)_{f1}-(CH_2)_{g1}-$$

wherein: Q, each independently at each occurrence, represents an oxygen atom, phenylene, carbazolylene, —NR— wherein R represents a hydrogen atom or an organic group, or a divalent polar group; Z, each independently at each occurrence, represents a hydrogen atom, a fluorine atom or a lower fluoroalkyl group; e1, f1 and g1 are each independently an integer of 0 or more and 50 or less; the sum of e1, f1 and g1 is at least 1; and the occurrence order of each repeating unit, which is shown in parenthesis, is not limited in the formula;

$R^{73}$ each independently represents a divalent organic group;

$R^{74}$, each independently at each occurrence, represents $R^{74a}$ or $R^{74b}$, provided that at least one $R^{74}$ is $R^{74a}$;

$R^{74a}$, each independently at each occurrence, represents a divalent organic group having a polymerizable group;

$R^{74b}$, each independently at each occurrence, represents a divalent organic group not having a polymerizable group;

n10 is each independently an integer of 1 or more and 50 or less;

$R^{75}$ each independently represents —O—, —S—, —NH— or a single bond; and $R^{76}$ each independently represents a monovalent organic group or a hydrogen atom.

When used in the present specification, the "monovalent organic group" and the "divalent organic group" mean monovalent and divalent groups containing carbon, respectively.

In the above-described formulae (A1) and (A2), $R^{71}$ each independently represents a polymerizable group.

$R^7$ is preferably a group represented by the following formula:

$$-R^{63}-CR^{64}=CH_2$$

wherein $R^{63}$ is a single bond, —O—, —CO— or —OC(O)—; and $R^{64}$ represents a hydrogen atom, a fluorine atom, an alkyl group having 1 to 10 carbon atoms (preferably an alkyl group having 1 to 3 carbon atoms, and more preferably a methyl group), a lactam group (preferably a β-lactam, γ-lactam or δ-lactam group, and more preferably a γ-lactam group) or a phenyl group wherein the alkyl group, the lactam group and the phenyl group are optionally substituted with a fluorine atom, and is preferably a methyl group or a hydrogen atom.

A more preferable polymerizable group is a group represented by the following formula:

$$-OC(O)-CR^{64}=CH_2$$

wherein $R^{64}$ is as defined above.

Further preferably, $R^{71}$ is an acryloyl group or a methacryloyl group.

In the above-described formulae (A1) and (B1), $Rf^a$ represents an alkyl group having 1 to 16 carbon atoms optionally substituted with one or more fluorine atoms.

In the above-described alkyl group having 1 to 16 carbon atoms optionally substituted with one or more fluorine atoms, the "alkyl group having 1 to 16 carbon atoms" may be linear or branched, and it is preferably a linear or branched alkyl group having 1 to 6 carbon atoms, particularly 1 to 3 carbon atoms, and more preferably a linear alkyl group having 1 to 3 carbon atoms.

In addition, $Rf^a$ is preferably an alkyl group having 1 to 16 carbon atoms substituted with one or more fluorine atoms, more preferably a $CF_2H-C_{1-15}$ fluoroalkylene group or perfluoroalkyl group, further preferably a perfluoroalkyl group having 1 to 16 carbon atom, and further more preferably a perfluoroalkyl group having 1 to 6 carbon atoms, particularly 1 to 3 carbon atoms.

In the above-described formulae (A1) and (A2), X each independently represents a divalent organic group. The X group is understood as a linker linking PFPE and $R^{71}$. Accordingly, the X group may be any divalent organic group as long as a compound represented by the above-described formulae (A1) and (A2) can be stably exist.

Examples of the above-described X are not limited, but it is preferably, for example, a group represented by the following formula:

$$-(CFZ')_x-(CH_2)_y-(Y')_z-$$

wherein

Z' represents a fluorine atom, or a perfluoroalkyl group having 1 to 3 carbon atoms or a derivative group thereof;

Y' represents —OCO—, —OCONH— or —CONH—, or an organic group containing one of them;

x, y and z are each independently an integer of 0 to 3; and the occurrence order of each repeating unit, which is shown in parenthesis subscripted with x, y or z, is not limited in the formula.

Specific examples of the above-described X include, for example:

$$-CF_2CF_2CH_2-$$

$$-CF_2CF_2CH_2-OCO-$$

$$-CF_2CF_2CH_2-CONH-$$

$$-CF_2CF_2CH_2-OCONH-$$

or the like.

In the above-described formulae (B1) and (B2), $R^{72}$ is a group represented by the formula: $-(Q)_{e1}-(CFZ)_{f1}-(CH_2)_{g1}-$, wherein: e1, f1 and g1 are each independently an integer of 0 or more and 50 or less; the sum of e1, f1 and g1 is at least 1; and the occurrence order of each repeating unit, which is shown in parenthesis, is not limited in the formula.

In the above-described formula, Q represents an oxygen atom, phenylene, carbazolylene, —NR— wherein R represents a hydrogen atom or an organic group, or a divalent polar group, and it is preferably an oxygen atom or a divalent polar group, and more preferably an oxygen atom.

Examples of the "divalent polar group" in the above-described Q are not limited, but include —C(O)—, —C(=NR$^h$)— and —C(O)NR$^h$—, wherein R$^h$ represents a hydrogen atom or a lower alkyl group. The "lower alkyl group" is, for example, an alkyl group having 1 to 6 carbon atoms, for example, methyl, ethyl or n-propyl, and these are optionally substituted with one or more fluorine atoms.

In the above-described formula, Z represents a hydrogen atom, a fluorine atom or a lower fluoroalkyl group, and is preferably a fluorine atom.

The above-described "lower fluoroalkyl group" is, for example, a fluoroalkyl group having 1 to 6 carbon atoms, preferably 1 to 3 carbon atoms, preferably a perfluoroalkyl group having 1 to 3 carbon atoms, more preferably a trifluoromethyl group or a pentafluoroethyl group, and further preferably a trifluoromethyl group.

$R^{72}$ is preferably a group represented by the formula: —$(O)_{e1}$—$(CF_2)_{f1}$—$(CH_2)_{g1}$—, wherein e1, f1 and g1 are as defined above, and the occurrence order of each repeating unit, which is shown in parenthesis, is not limited in the formula.

Examples of the group represented by the above-described formula: —$(O)_{e1}$—$(CF_2)_{f1}$—$(CH_2)_{g1}$— include, for example, a group represented by —$(O)_{e'}$—$(CF_2)_{f'}$—$(CH_2)_{g'}$—O—$[(CH_2)_{g''}$—O—$]_{g'''}$, wherein e' is 0 or 1, f', g' and g'' are each independently an integer of 1 to 10, and g''' is 0 or 1.

In the above-described formulae (B1) and (B2), $R^{73}$ represents a divalent organic group.

The $R^{73}$ group is preferably —$C(R^{73a})(R^{73b})$—, wherein: $R^{73a}$ and $R^{73b}$ each independently represent a hydrogen atom or an alkyl group, and either $R^{73a}$ or $R^{73b}$ is preferably an alkyl group.

In the above-described formulae (B1) and (B2), $R^{74}$, each independently at each occurrence, are $R^{74a}$ or $R^{74b}$, provided that at least one $R^{74}$ is $R^{74a}$.

The above-described $R^{74a}$, each independently at each occurrence, represents a divalent organic group having a polymerizable group.

$R^{74a}$ is preferably a group represented by the following formula:

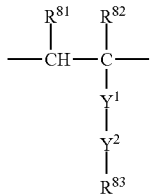

In the above-described formula, $R^{81}$, each independently at each occurrence, represents a hydrogen atom or an alkyl group. The $R^{81}$ is preferably a hydrogen atom.

In the above-described formula, $R^{82}$, each independently at each occurrence, represents a hydrogen atom or an alkyl group. The $R^{82}$ is preferably a methyl group or a hydrogen atom, and is more preferably a hydrogen atom.

The above-described formula, $R^{83}$, each independently at each occurrence, represents an organic group having a polymerizable group.

Examples of such a polymerizable group include those equivalent to the above-described ones, but it is preferably $CH_2$=$CX^1$—$C(O)$—, wherein $X^1$ represents a hydrogen atom, a halogen atom such as a chlorine atom, a fluorine atom, or an alkyl group having 1 to 10 carbon atoms optionally substituted with fluorine, and specific examples thereof include $CH_2$=$C(CH_3)$—$C(O)$— or $CH_2$=$CH$—$C(O)$—.

In the above-described formula, $Y^1$ represents —O—, —$N(R^f)$—, phenylene or carbazolylene, wherein $R^f$ represents an organic group, and is preferably an alkyl group.

$Y^1$ is preferably —O—, phenylene or carbazolylene, more preferably —O— or phenylene, and further preferably —O—.

In the above-described formula, $Y^2$ represents a linker whose backbone has 1 to 16 (more preferably 2 to 12, and further preferably 2 to 10) carbon atoms. Examples of the $Y^2$ are not limited, but include, for example, —$(CH_2$—$CH_2$—$O)_{p10}$—, wherein p10 represents an integer of 1 to 10, for example, an integer of 2 to 10, —$(CHR^g)_{p20}$—O—, wherein p20 is an integer of 1 to 40 and $R^g$ represents hydrogen or a methyl group, —$(CH_2$—$CH_2$—$O)_{p30}$—CO—NH—$CH_2$—$CH_2$—O—, wherein p30 represents an integer of 1 to 10, for example, an integer of 2 to 10, —$CH_2$—$CH_2$—O—$CH_2$—$CH_2$—, —$(CH_2)_{p40}$—, wherein p40 represents an integer of 1 to 6, —$(CH_2)_{p50}$—O—CONH—$(CH_2)_{p60}$—, wherein p50 represents an integer of 1 to 8, preferably 2 or 4 and p60 represents an integer of 1 to 6, preferably 3, or —O—, provided that $Y^1$ is not —O—. Preferable examples of $Y^2$ include —$(CH_2$—$CH_2$—$O)_{p10}$—, wherein p10 represents an integer of 1 to 10, for example, an integer of 2 to 10, or —$(CHR^d)_{p20}$—O—, wherein p20 is an integer of 1 to 40 and $R^d$ represents hydrogen or a methyl group, and specific examples thereof include —$(CH_2$—$CH_2$—$O)_2$— or —$CH_2$—$CH_2$—O—. It is noted that, in these groups, the left end is bonded to the side of the molecular backbone (the side of $Y^1$) and the right end is bonded to the side of the polymerizable group (the side of $R^{83}$).

$R^{74a}$ is further preferably a group represented by the following formula:

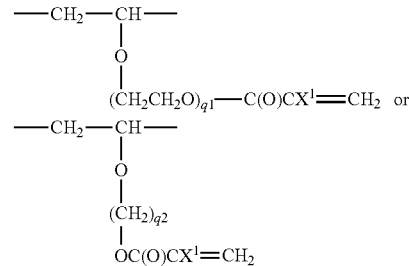

In the above-described formula, $X^1$ represents a hydrogen atom, a halogen atom such as a chlorine atom and a fluorine atom, or an alkyl group having 1 to 10 carbon atoms optionally substituted with fluorine, and is preferably a hydrogen atom or an alkyl group having 1 to 10 carbon atoms such as a methyl group. In the above-described formula, q1 is an integer of 1 to 10, and preferably an integer of 1 to 5 such as 1 or 2. q2 is an integer of 1 to 10, and preferably an integer of 1 to 5, for example 2.

The above-described $R^{74b}$, each independently at each occurrence, is a divalent organic group not having a polymerizable group.

$R^{74b}$ is preferably —$(CHR^{74c}$—$CR^{74d}R^{74e})_s$—, wherein: $R^{74c}$ and $R^{74d}$ each independently represent a hydrogen atom or an alkyl group; s is an integer of 0 to 50; and $R^{74e}$ is -Q'-$R^{74f}$, wherein Q' is as defined for Q, $R^{74f}$ is an organic group not having a polymerizable group, and is a group that a $R^{74g}$ group described later is bonded via a linker or directly to Q'.

The linker is preferably as follows:
(a) —$(CH_2$—$CH_2$—$O)_{s1}$—, wherein s1 represents an integer of 1 to 10, for example, an integer of 2 to 10;
(b) —$(CHR^{74h})_{s2}$—O—, wherein s2 represents the number of repetitions, which is an integer of 1 to 40, and $R^{74h}$ represents hydrogen or a methyl group;
(c)  —$(CH_2$—$CH_2$—$O)_{s1}$—CO—NH—$CH_2$—$CH_2$—O—, wherein s1 is as defined above;
(d) —$CH_2$—$CH_2$—O—$CH_2$—$CH_2$—;
(e) —$(CH_2)_{s3}$—, wherein s3 represents an integer of 1 to 6;
(f) —$(CH_2)_{s4}$—O—CONH—$(CH_2)_{s5}$—, wherein s4 represents an integer of 1 to 8, preferably 2 or 4, and s5 represents an integer of 1 to 6, preferably 3; or (g) —O—, provided that Q' is not —O—.
R$^{74g}$ is preferably the following group:
(i) an alkyl group
Examples: methyl and ethyl;
(ii) a chain group containing an alkyl group substituted with fluorine
Examples:

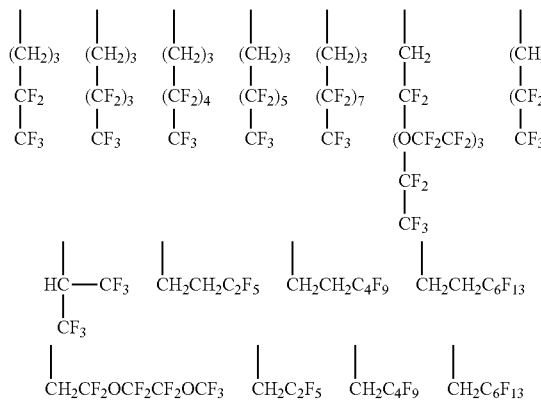

(iii) a group containing one or more cyclic moieties selected from the group consisting of a monocyclic carbocycle, a bicyclic carbocycle, a tricyclic carbocycle and a tetracyclic carbocycle
Examples:

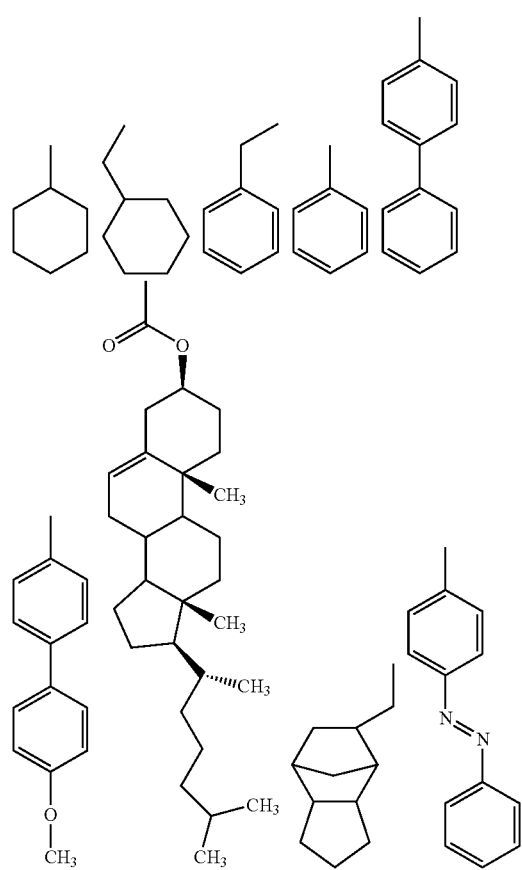

(iv) a group containing a hydrocarbon group substituted with one or more (preferably one or two) carboxy groups
Examples:

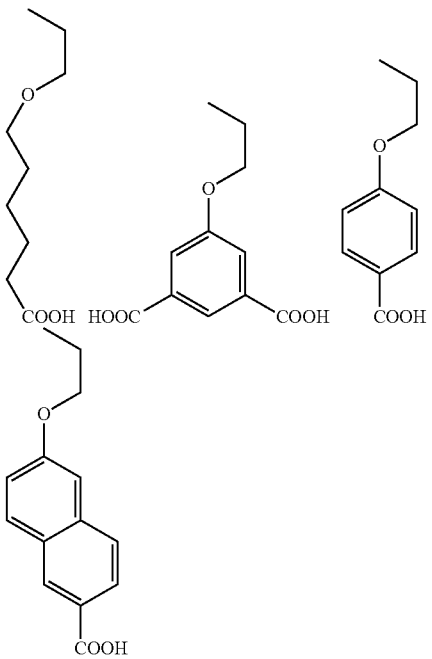

(v) a group containing one or more (preferably one) amino groups;
(vi) a hydrogen atom; or
(vii) a group containing an imidazolium salt
Examples:

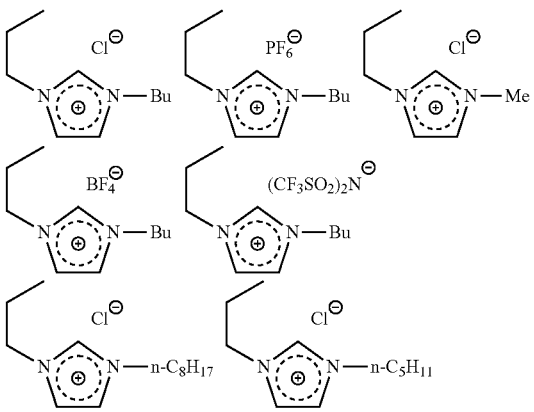

R$^{74g}$ is more preferably a hydrogen atom or an alkyl group that may be fluorinated and bonded via an ethylene chain; more preferably a hydrogen atom, a methoxyethyl group, an isobutyl group or R$^{31}$—CF$_2$—(CF$_2$)$_{s6}$—(CH$_2$)$_{s7}$—O—(CH$_2$)$_2$—, wherein R$^{31}$ is a fluorine atom or a hydrogen atom, s6 is an integer of 0 to 6, and s7 is an integer of 1 to 6; and further preferably a 3-(perfluoroethyl) propoxyethyl group [rational formula: CF$_3$—(CF$_2$)—(CH$_2$)$_3$—O—(CH$_2$)$_2$—].

In the above-described R$^{74}$, the constituent unit R$^{74a}$ and the constituent unit R$^{74b}$ may each form a block or may be bonded randomly.

In the above-described formulae (B1) and (B2), n10 is an integer of 1 or more and 100 or less, preferably an integer of 1 or more and 50 or less, and further preferably an integer of 2 or more and 30 or less.

In the above-described formulae (B1) and (B2), $R^{75}$ represents —O—, —S—, —NH— or a single bond, and is preferably —O—.

In the above-described formulae (B1) and (B2), $R^{76}$ represents a monovalent organic group or a hydrogen atom.

$R^{76}$ is preferably $Rf^a$—PFPE—$R^{72}$, wherein $Rf^a$, PFPE and $R^{72}$ are as defined above, or an alkyl group having 1 to 10 carbon atoms optionally substituted with fluorine, more preferably an alkyl group having 1 to 6 carbon atoms, and further preferably methyl.

In one embodiment, compounds represented by the above-described formulae (B1) and (B2) may be at least one compound represented by the following general formulae (B1a) and (B2a), respectively:

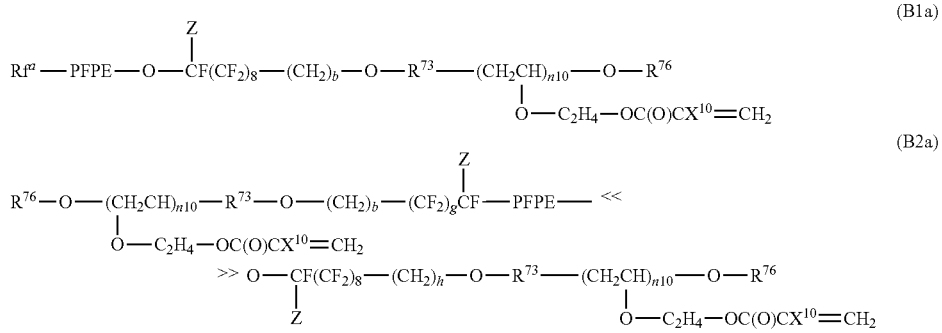

wherein $Rf^a$, PFPE, $R^{73}$, $R^{76}$, $X^{10}$, Z and n10 are as defined above;
g is 0 or 1; and
h is 1 or 2.

Another example of the fluorine-containing monomer is a compound represented by:

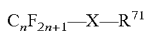

$C_nF_{2n+1}$—X—$R^{71}$ wherein $R^{71}$ and X are as defined above; and
n is an integer of 1 to 30, and preferably an integer of 3 to 20 such as an integer of 4 to 10.

Still another example of the fluorine-containing monomer is a fluorine-containing acrylate ester represented by the formula:

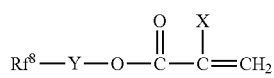

wherein X is a hydrogen atom, a methyl group, a fluorine atom, a chlorine atom, a bromine atom, an iodine atom, a $CFX^{11}X^{12}$ group (provided that $X^{11}$ and $X^{12}$ are, independently of each other, a hydrogen atom, a fluorine atom, a chlorine atom, a bromine atom or an iodine atom), a cyano group, a linear or branched fluoroalkyl group having 1 to 21 carbon atoms, a substituted or unsubstituted benzyl group, or a substituted or unsubstituted phenyl group;

Y is an aliphatic group having 1 to 10 carbon atoms, an aromatic group or cycloaliphatic group having 6 to 10 carbon atoms, a —$CH_2CH_2N(R)SO_2$— group (provided that R is an alkyl group having 1 to 4 carbon atoms), or a —$CH_2CH(OY^1)CH_2$— group (provided that $Y^1$ is a hydrogen atom or an acetyl group); and $Rf^8$ is a linear or branched fluoroalkyl group or fluoroalkenyl group having 1 to 6 carbon atoms.

In the fluorine-containing acrylate ester, X is preferably a hydrogen atom or a methyl group.

In the above-described formula, the $Rf^8$ group is preferably a perfluoroalkyl group or a perfluoroalkenyl group. The number of carbons in the fluoroalkyl group or the fluoroalkenyl group is 1 to 6, for example 1 to 4.

Examples of the fluoroalkyl group include: —$CF_3$, —$CF_2CF_3$, —$CF_2CF_2CF_3$, —$CF(CF_3)_2$, —$CF_2CF_2CF_2CF_3$, —$CF_2CF(CF_3)_2$, —$C(CF_3)_3$, —$(CF_2)_4CF_3$, —$(CF_2)_2CF(CF_3)_2$, —$CF_2C(CF_3)_3$, —$CF(CF_3)CF_2CF_2CF_3$, —$(CF_2)_5CF_3$, —$(CF_2)_3CF(CF_3)_2$ and the like.

Examples of the fluoroalkenyl group include: —CF=$CF_2$, —$CF_2$CF=$CF_2$, —$(CF_2)_2$CF=$CF_2$, —$CF_2$C($CF_3$)=$CF_2$, —CF($CF_3$)CF=$CF_2$, —$(CF_2)_3$CF=$CF_2$, —C($CF_3$)$_2$CF=$CF_2$, —$(CF_2)_2$C($CF_3$)=$CF_2$, —$(CF_2)_4$CF=$CF_2$, —$(CF_2)_4$CF=$CF_2$, —$(CF_2)_3$C($CF_3$)=$CF_2$, and the like.

Y is an aliphatic group having 1 to 10 carbon atoms, an aromatic group or cycloaliphatic group having 6 to 10 carbon atoms, a —$CH_2CH_2N(R)SO_2$— group (provided that R is an alkyl group having 1 to 4 carbon atoms), or a —$CH_2CH(OY^1)CH_2$— group (provided that $Y^1$ is a hydrogen atom or an acetyl group). The aliphatic group is preferably an alkylene group (in particular, that having 1 to 4, for example 1 or 2 carbon atoms). The aromatic group and the cycloaliphatic group may be either substituted or not substituted.

Examples of the fluorine-containing monomer may include a fluorine-containing acrylate ester indicated by the formula:

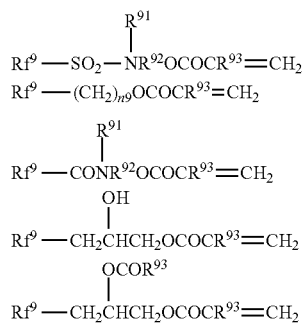

-continued

Rf$^9$—O—Ar—CH$_2$OCOCR$^{93}$=CH$_2$ wherein
Rf$^9$ represents a perfluoroalkyl group having 1 to 6 carbon atoms;
R$^{91}$ is preferably a hydrogen atom or an alkyl group having 1 to 10 carbon atoms;
R$^{92}$ represents an alkylene group having 1 to 10 carbon atoms;
R$^{93}$ represents a hydrogen atom or a methyl group;
Ar represents an aryl group optionally having a substituent; and
n9 represents an integer of 1 to 10.

In one embodiment, in the above-described formula, Rf$^9$ is preferably a perfluoroalkyl group having 1 to 10 carbon atoms;
R$^{91}$ is preferably a hydrogen atom or an alkyl group having 1 to 10 carbon atoms;
R$^{92}$ is preferably an alkylene group having 1 to 10 carbon atoms;
R$^{93}$ is preferably a hydrogen atom or a methyl group;
Ar is preferably an aryl group optionally having a substituent; and
n9 is preferably an integer of 1 to 10.

Specific examples of the fluorine-containing monomer may include:
CF$_3$(CH$_2$)OCOCH=CH$_2$,
CF$_3$(CH$_2$)OCOC(CH$_3$)=CH$_2$,
CF$_3$(CF$_2$)$_5$(CH$_2$)OCOCH=CH$_2$,
CF$_3$(CF$_2$)$_5$(CH$_2$)OCOC(CH$_3$)=CH$_2$,
CF$_3$(CF$_2$)$_7$(CH$_2$)OCOCH=CH$_2$,
CF$_3$(CF$_2$)$_7$(CH$_2$)OCOC(CH$_3$)=CH$_2$,
(CF$_3$)$_2$CF(CF$_2$)$_3$(CH$_2$)$_2$OCOCH=CH$_2$,
CF$_3$(CF$_2$)$_3$(CH$_2$)$_2$OCOC(CH$_3$)=CH$_2$,
CF$_3$(CF$_2$)$_3$(CH$_2$)$_2$OCOCH=CH$_2$,
CF$_3$(CF$_2$)$_5$(CH$_2$)$_2$OCOC(CH$_3$)=CH$_2$,
CF$_3$(CF$_2$)$_5$(CH$_2$)$_2$OCOCH=CH$_2$,
CF$_3$CF$_2$(CH$_2$)$_2$OCOCH=CH$_2$,
CF$_3$(CF$_2$)$_3$SO$_2$N(CH$_3$)(CH$_2$)$_2$OCOCH=CH$_2$,
CF$_3$(CF$_2$)$_3$SO$_2$N(C$_2$H$_5$)(CH$_2$)$_2$OCOC(CH$_3$)=CH$_2$,
(CF$_3$)$_2$CF(CF$_2$)$_3$CH$_2$CH(OCOCH$_3$)CH$_2$OCOC(CH$_3$)=CH$_2$,
(CF$_3$)$_2$CF(CF$_2$)$_3$CH$_2$CH(OH)CH$_2$OCOCH=CH$_2$.

In one embodiment, the fluorine-containing monomer has a perfluoroalkyl group and a polymerizable group A.

In the present embodiment, the above-described fluorine-containing monomer is preferably at least one selected from the group consisting of a compound represented by Rf′CH=CH$_2$, a perfluoroolefin, a dimer of a perfluoroolefin and an oligomer of a perfluoroolefin.

The above-described Rf′ is a perfluoroalkyl group, and preferably a linear perfluoroalkyl group having 1 to 10 carbon atoms. In particular, Rf′ is represented by F—(CF$_2$)$_n$, wherein n is an integer of 1 to 10, and more preferably, n is an integer of 4 to 8, for example 6.

Specific examples of the structure of the above-described compound represented by Rf′CH=CH$_2$ may include, for example, perfluorohexylethylene (F(CF$_2$)$_6$CH=CH$_2$).

Examples of a method for synthesizing the above-described compound represented by Rf′CH=CH$_2$ are not limited, but may include, for example, a method in which a halide represented by Rf′CH$_2$CH$_2$Y$^3$, wherein Rf′ has the same meaning as that described above and Y$^3$ is Br or I, and an alkaline metal salt of a carboxylic acid are heated in an alcohol solvent (for example, Japanese Patent Publication No. S39-18112). In the above-described method, the alcohol and the fluorine-containing monomer according to the present embodiment can be separated through a so-called crystallization operation, focusing on the difference between the melting points of the alcohol and the fluorine-containing monomer (for example, a method for separating an olefin-alcohol azeotrope described in Japanese Patent Laid-Open No. 2009-173588).

Examples of the above-described perfluoroolefin may include, for example, tetrafluoroethylene and hexafluoropropene.

Examples of the dimer of a perfluoroolefin or the oligomer of a perfluoroolefin may include, for example, an oligomer of tetrafluoroethylene, an oligomer of hexafluoropropylene and the like. The above-described oligomer of tetrafluoroethylene preferably has a degree of polymerization of 2 to 7, and the oligomer of hexafluoropropylene preferably has a degree of polymerization of 2 to 4. These oligomers are advantageous from the viewpoint where they can be applied to a variety of processing treatments. The oligomer of tetrafluoroethylene or the oligomer of hexafluoropropylene can be obtained by oligomerizing tetrafluoroethylene or hexafluoropropylene with a method described in, for example, U.S. Pat. No. 3,403,191 or 2,918,501.

The above-described oligomer may be a compound having highly branched molecular chains, composed of many isomers. The above-described oligomer may have, for example, a structure as described below:

Dimer of hexafluoropropene:

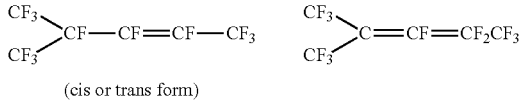

(cis or trans form)

Trimer of hexafluoropropene:

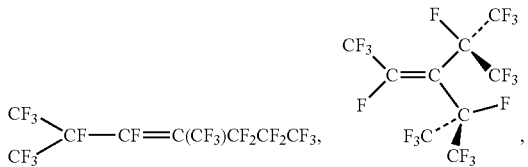

(cis or trans form)

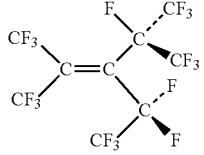

Tetramer of hexafluoropropene:

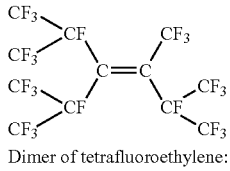

Dimer of tetrafluoroethylene:

CF$_3$CF=CFCF$_3$

Trimer of tetrafluoroethylene:

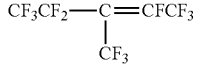

Tetramer of tetrafluoroethylene:

-continued

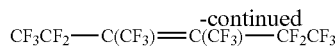

(cis or trans form)

Pentamer of tetrafluoroethylene:

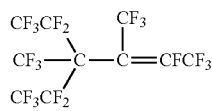

Hexamer of tetrafluoroethylene:

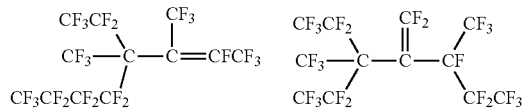

In one embodiment, the above-described fluorine-containing monomer is a compound represented by $Rf^7CH=CH_2$.

In one embodiment, the above-described fluorine-containing monomer is at least one selected from the group consisting of a perfluoroolefin, a dimer of a perfluoroolefin and an oligomer of a perfluoroolefin.

In another embodiment, the fluorine-containing monomer may be a compound having an ethylenic double bond wherein a part of or all hydrogen atoms of a hydrocarbon are substituted with fluorine atoms.

Examples of the above-described compound having an ethylenic double bond wherein a part of or all hydrogen atoms of a hydrocarbon are substituted with fluorine atoms may include, for example, a reactive olefinic monomer, which is fluorinated, has a alkyl group having 1 to 6 carbon atoms, has no ester group and has an ethylenic double bond, specifically ethylene, propylene, butylene and the like, or a dimer thereof. The above-described compound is preferably a reactive olefinic monomer which has a perfluoroalkyl group having 1 to 6 carbon atoms, has no ester group, and has an ethylenic double bond, specifically perfluoro-substituted ethylene, propylene, butylene and the like, or a dimer thereof. In a preferable embodiment, a hydrocarbon having an ethylenic double bond wherein a part of or all hydrogen atoms of the hydrocarbon are substituted with fluorine atoms may be tetrafluoroethylene, hexafluoropropylene, a dimer of hexafluoropropylene, or a reactive olefinic monomer having an ethylenic double bond which has a perfluoroalkyl group having 1 to 6 carbon atoms and has no ester group.

In a preferable embodiment, the fluorine-containing monomer comprises at least one selected from the group consisting of a fluorine-containing acrylate ester represented by the formula:

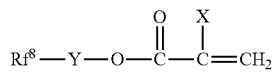

wherein X, Y and $Rf^8$ are as defined above, a compound represented by $Rf^7CH=CH_2$ wherein $Rf^7$ is a perfluoroalkyl group, and a perfluoroolefin. Preferably, X is a hydrogen atom or a methyl group; Y is an aliphatic group having 1 to 10 carbon atoms, an aromatic group or cycloaliphatic group having 6 to 10 carbon atoms, a $—CH_2CH_2N(R)SO_2—$ group (provided that R is an alkyl group having 1 to 4 carbon atoms), or a $—CH_2CH(OY^1)CH_2—$ group (provided that $Y^1$ is a hydrogen atom or an acetyl group); and the $Rf^8$ group is a perfluoroalkyl group or perfluoroalkenyl group having 1 to 6 carbon atoms, and more preferably 1 to 4 carbon atoms.

In one embodiment, the above-described monomer is a monomer free of fluorine atom (hereinafter, may also be referred to as "fluorine-free monomer").

In one embodiment, the above-described fluorine-free monomer may be a compound having a polymerizable group B and free of fluorine atom.

The polymerizable group B is preferably a group represented by the following formula:

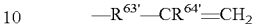

wherein
$R^{63'}$ is a single bond or $—OC(O)—$; and
$R^{64'}$ represents a hydrogen atom, or an alkyl group having 1 to 10 carbon atoms (preferably an alkyl group having 1 to 3 carbon atoms, and more preferably a methyl group) or a phenyl group, and is preferably a methyl group or a hydrogen atom.

A more preferable polymerizable group B is a group represented by the following formula:

wherein $R^{64'}$ is as defined above.

A further preferable polymerizable group B is an acryloyl group or a methacryloyl group.

Examples of a compound having the polymerizable group B may include, for example, (meth)acrylic monomers in which an alkyl group having 1 to 20 carbon atoms is bonded to the ester terminal; and vinyl monomers such as vinylnorbornene, styrene and vinyl chloride.

Examples of the compound having the polymerizable group B may include, for example, (meth)acrylic monomers in which an alkyl group having 1 to 15 carbon atoms is bonded to the ester terminal, specifically, stearyl (meth)acrylate, isobornyl (meth)acrylate, cyclohexyl (meth)acrylate, (meth)acrylic acid, vinyl acetate, hydroxyethyl (meth)acrylate, hydroxypropyl (meth)acrylate, methyl (meth)acrylate, ethyl (meth)acrylate, butyl (meth)acrylate, ethylene glycol dimethacrylate, N,N-dimethylaminoethyl acrylate, decyl (meth)acrylate, dodecyl (meth)acrylate, dodecenyl (meth)acrylate, tetradecyl (meth)acrylate, tetradecenyl (meth)acrylate and the like; acrylamide, N,N-dimethyl acrylamide, N,N-dimethylaminopropyl acrylamide; vinyl monomers such as vinyl propionate, (meth)acrylonitrile, vinylnorbornene, styrene and vinyl chloride; and the like.

In another embodiment, from the viewpoint of increasing the grafting amount, a polyfunctional (meth)acrylate may be used as the above-described compound having the polymerizable group B. The polyfunctional (meth)acrylate is as defined above.

In one embodiment, the polymerizable group B is a group represented by:

wherein
$R^{63'}$ is a single bond; and
$R^{64'}$ represents a hydrogen atom, or an alkyl group having 1 to 10 carbon atoms (preferably an alkyl group having 1 to 5 carbon atoms, and more preferably a methyl group) or a phenyl group, and is preferably a methyl group or a hydrogen atom.

In the present embodiment, examples of the above-described compound having the polymerizable group B may include a compound in which, for example, an alkyl group having 1 to 12 carbon atoms, specifically an alkyl group having 1 to 10 carbon atoms, and more specifically an alkyl group having 3 to 10 carbon atoms is bonded to the above-described polymerizable group B.

In the present embodiment, examples of the above-described compound having the polymerizable group B may include, for example, 1-hexene, 1-octene, 1-decene, 1-dodecene, isobutene, pentene, heptene, nonene and the like.

The above-described monomer preferably has an ethylenic double bond.

In one embodiment, the above-described monomer comprises at least one fluorine-containing monomer.

The above-described fluorine atom-containing monomer is preferably a so-called perfluoromonomer in which all hydrogen atoms are substituted with fluorine atoms.

In these fluorine-containing monomers, one or more fluorine atoms are optionally substituted with one or more other substituents.

In a preferable embodiment, the above-described fluorine-containing monomer is a monomer represented by the following formula:

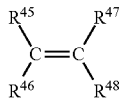

wherein
$R^{45}$ is a hydrogen atom, a halogen atom, or an alkyl group optionally substituted with a halogen atom;
$R^{46}$ is a hydrogen atom, a halogen atom, or an alkyl group optionally substituted with a halogen atom;
$R^{47}$ is a hydrogen atom, a halogen atom, or an alkyl group optionally substituted with a halogen atom;
$R^{48}$ is a hydrogen atom, a halogen atom, —$R^{37}$, —$R^{38}$—O—$R^{37}$, —$R^{38}$—COOR$^{37}$, —$R^{38}$—OCOR$^{37}$, or aryl;
$R^{37}$ is a hydrogen atom, a halogen atom, an alkyl group optionally substituted with a halogen atom, or an aryl group optionally substituted with a halogen atom; and
$R^{38}$ is a single bond or an alkylene group optionally substituted with a halogen atom,
provided that in the formula, at least one fluorine atom is included.

In the above-described formula, the alkyl group is preferably an alkyl group having 1 to 6 carbon atoms, more preferably an alkyl group having 1 to 3 carbon atoms, and further preferably a methyl group.

In the above-described formula, the alkylene group is preferably an alkylene group having 1 to 6 carbon atoms, and more preferably an alkylene group having 1 to 3 carbon atoms.

In the above-described formula, the aryl group is preferably an aryl group having 6 to 22 carbon atoms, and more preferably a phenyl group.

In the above-described formula, the halogen atom is preferably a fluorine atom, a chlorine atom, a bromine atom or an iodine atom, more preferably a fluorine atom or a chlorine atom, and further preferably a fluorine atom.

In a preferable embodiment, $R^{48}$ is a fluorine atom, an alkyl group having 1 to 3 carbon atoms optionally substituted with a fluorine atom, an alkoxy group having 1 to 3 carbon atoms optionally substituted with a fluorine atom, an aryl group having 6 to 22 carbon atoms optionally substituted with a fluorine atom, or —COOR$^{37}$ optionally substituted with a fluorine atom, and is an aryl group optionally substituted with a fluorine atom.

Examples of the above-described fluorine-containing monomer include, for example, styrene having a fluorine atom or a substituent containing a fluorine atom in a phenyl group, such as 2,3,4,5,6-pentafluorostyrene and trifluoromethylstyrene.

In another embodiment, examples of the fluorine-containing monomer include, for example, monofluoroethylene, 1,1-difluoroethylene, 1,3-difluoroethylene, trifluoroethylene, tetrafluoroethylene (TFE), 1,1,1,2-tetrafluoro-2-propylene, hexafluoropropylene (HFP), perfluoro(alkyl vinyl ether) (PAVE), chlorotrifluoroethylene (CTFE), vinylidene fluoride (VDF), and the like.

In one embodiment, the above-described monomer comprises at least one fluorine-free monomer.

Examples of the above-described fluorine-free monomer include, for example, (meth)acrylic acid, (meth)acrylic acid ester, styrene, vinyl acetate, vinyl chloride, vinylidene chloride, 1,3-butadiene, and the like.

In these fluorine-free monomers, one or more hydrogen atoms are optionally substituted with one or more other substituents.

In one embodiment, the above-described fluorine-free monomer is a compound represented by the following formula:

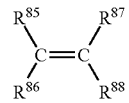

wherein
$R^{85}$ is a hydrogen atom, a chlorine atom, or an alkyl group optionally substituted with a chlorine atom;
$R^{86}$ is a hydrogen atom, a chlorine atom, or an alkyl group optionally substituted with a chlorine atom;
$R^{87}$ is a hydrogen atom, a chlorine atom, or an alkyl group optionally substituted with a chlorine atom;
$R^{88}$ is a hydrogen atom, a chlorine atom, —$R^{89}$, —$R^{90}$—O—$R^{89}$, —$R^{90}$—COOR$^{89}$, —$R^{80}$—OCOR$^{89}$, an aryl group, or —CHCH$_2$;
$R^{89}$ is a hydrogen atom, a chlorine atom, an alkyl group optionally substituted with a chlorine atom, or an aryl group optionally substituted with a chlorine atom; and
$R^{90}$ is a single bond or an alkylene group optionally substituted with a chlorine atom.

In a preferable embodiment, $R^{88}$ is aryl, a hydrogen atom, an alkyl group having 1 to 3 carbon atoms optionally substituted with a chlorine atom, an alkoxy group having 1 to 3 carbon atoms optionally substituted with a chlorine atom, an aryl group having 6 to 22 carbon atoms optionally substituted with a chlorine atom, —COOR$^{75}$ optionally substituted with a chlorine atom, or —CHCH$_2$.

Examples of the above-described fluorine-free monomer include, for example, (meth)acrylic acid, (meth)acrylic acid ester, styrene, vinyl acetate, vinyl chloride, vinylidene chloride, 1,3-butadiene, and the like.

When a conjugated diene-based monomer such as the above-described 1,3-butadiene is used, the obtained polymer chain may have a double bond in the backbone of the polymer chain, or may have a double bond in the side chain. For example, when 1,3-butadiene is used as a monomer, the polymer chain may have either or both of —(CH$_2$CH=CHCH$_2$)— and —(CH$_2$CH(CH=CH$_2$))— units.

The double bonds present in the above-described polymer chain can also serve as reactive sites. For example, reaction with Rf$^\alpha$-Hal wherein Rf$^\alpha$ is a fluoroalkyl, and Hal is a halogen, such as bromine or iodine, can yield —(CH$_2$—CHHal-CHRf$^\alpha$—CH$_2$)— or —(CH$_2$CH(CHHal-CH$_2$Rf$^\alpha$))—.

The conditions for the above-described living radical polymerization are not limited, and can be appropriately selected by those having ordinary skill in the art depending on the raw materials used and the desired product.

The above-described polymerization reaction is preferably performed in the presence of a radical generator.

Examples of the above-described radical generator include, for example, organic peroxides, inorganic peroxides, organic azo compounds, and the like, of which organic peroxides are preferably used. Examples include, but are not limited to, benzoyl peroxide as the organic peroxide, potassium persulfite as the inorganic peroxide, and azobisisobutyronitrile (AIBN) as the organic azo compound, and the like.

A Polymer obtained from the compound represented by any of formulae (1) to (4) and the monomer of the present disclosure comprises the polymer represented by any of the following formulae (1A) to (4A):

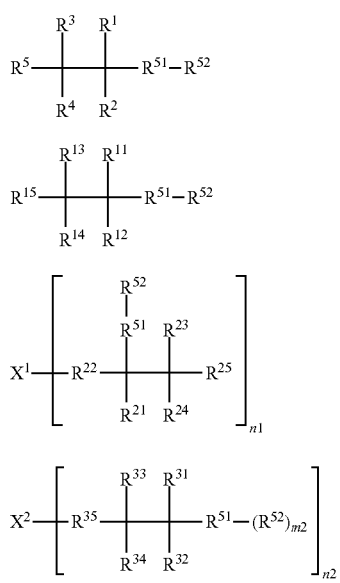

wherein
R$^1$, R$^2$, R$^3$, R$^4$, R$^5$, R$^{11}$, R$^{12}$, R$^{13}$, R$^{14}$, R$^{15}$, X$^1$, n1, R$^{21}$, R$^{22}$, R$^{23}$, R$^{24}$, R$^{25}$, X$^2$, n2, R$^{31}$, R$^{32}$, R$^{33}$, R$^{34}$, and R$^{35}$ are as defined above;
R$^{51}$, each independently at each occurrence, is a polymer chain;
R$^{52}$, each independently at each occurrence, is an iodine atom or a hydrogen atom; and
m2, each independently at each occurrence, is any integer.

In the above-described formula, the polymer chain in R$^{51}$ means a chain in which at least 2, preferably at least 5, preferably at least 20 units derived from one or more above-described monomers are bonded.

In one embodiment, R$^{51}$ is a divalent polymer chain, and m2 is 1.

In addition, the present disclosure provides a mixture of a polymer of the above-described formula (4A) and a polymer by-product in which R$^{52}$ in formula (4A) is a group derived from a radical generator or a group derived from a polymerization solvent. Such a mixture may comprise 80 mol % or more, 90 mol % or more, 95 mol % or more, or 98 mol % or more of the polymer represented by formula (4A), and comprise a polymer by-product as the rest.

The present disclosure also provides an inorganic particle comprising a compound containing I—CR$^x{}_2$—COO—, wherein R$^x$ is an optional substituent, on a surface thereof.

In one embodiment, the present disclosure provides an inorganic particle containing SiO$_2$ as a main component and having a compound represented by the following formula (5) on a surface thereof:

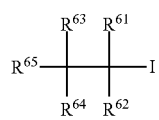

wherein
R$^{61}$ is H, F, Cl, CH$_3$, CF$_3$, or O(CF$_2$)$_{p5}$F;
R$^{62}$ is —COOR$^{66}$;
R$^{63}$ is H or F;
R$^{64}$ is H or F;
R$^{65}$ is H, F, or an alkyl group optionally substituted with fluorine;
R$^{66}$ is a single bond or —R$^{67}$—R$^{68}$;
R$^{67}$ is an alkylene group optionally substituted with fluorine or a (poly)alkyleneoxy group;
R$^{68}$ is a single bond, —O—, or —SiR$^{69}{}_u$R$^{70}{}_{3-u}$;
R$^{69}$ is a single bond;
R$^{70}$ is each independently a hydrogen atom, an alkyl group, or an alkoxy group;
u is an integer of 1 to 3; and
p5 is an integer of 1 to 10.

The present disclosure provides a composition comprising the compound represented by any of formula (1) to (4), the polymer represented by any of formula (1A) to (4A), or the inorganic particle having the compound represented by formula (5) on a surface thereof described above.

EXAMPLES

Example 1

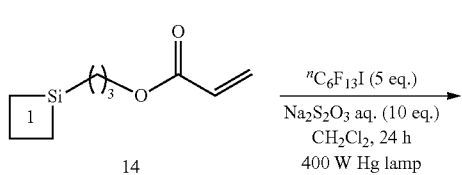

In a Pyrex tube, Compound 14 (279 mg) was dissolved in CH$_2$Cl$_2$ (0.4 ml), C$_6$F$_{13}$I (330 μL) and an aqueous sodium thiosulfate solution (474 mg, 2 ml aqueous solution) were added thereto, and the mixture was irradiated with ultraviolet ray for 24 hours using a 400 W high-pressure mercury lamp while keeping the temperature of the reaction system constant. After completion of the reaction, the reaction mixture was purified by column chromatography to give Compound 15 (429 mg).

$^1$H NMR (400 MHz, CDCl$_3$); 4.6 (1H, dd, J=3.6, 10.4 Hz, ICH), 4.2 (2H, t, OCH$_2$), 3.33 (1H, m, CF$_2$CHH), 2.71 (1H, m, CF$_2$CHCH), 1.88 (7H, m, CH(CH$_3$)$_2$), 1.78 (2H, tt, SiCH$_2$CH$_2$), 0.97 (21H, d, CH(CH$_3$)$_2$), 0.68 (2H, tt, CH$_2$CH$_2$CH$_2$), 0.63 (14H, SiCH$_2$CH) $^{19}$F NMR (376 MHz, CDCl$_3$); −81.3 (3F, s, CF$_3$), −114.7 (2F, dd, J=276.0, 670.4 Hz, CH$_2$CF$_2$), −122.3 (2F, s, CF$_2$), −123.4 (2F, s, CF$_2$), −124.1 (2F, s, CF$_2$), −126.6 (2F, s, CF$_2$)

Example 2

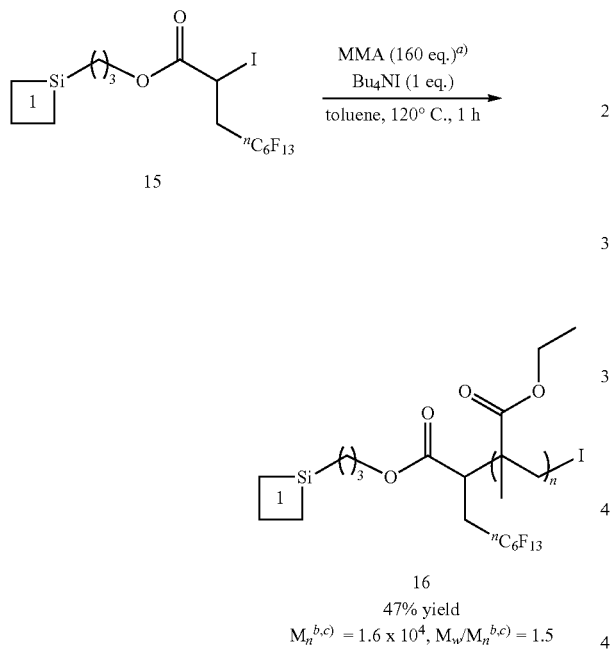

16
47% yield
$M_n^{b,c)} = 1.6 \times 10^4$, $M_w/M_n^{b,c)} = 1.5$ a) solution polymerization, 25% toluene and 75% monomer
b) MeOH-insoluble fraction
c) GPC measurement in THF (linear polystyrene as calibration standard)

In a reaction vessel, Compound 15 (0.1 mmol) was dissolved in toluene (0.57 mL), methyl methacrylate (1.7 mL) and tetrabutylammonium iodide (36.6 mg) were added thereto, and the inside of the reaction vessel was sufficiently substituted with an inert gas, followed by heating at 120° C. for 1 hour. After completion of the reaction, the reaction mixture was purified by re-precipitation to give Compound 16 (811 mg, $M_n$=1.6×10$^4$, $M_w/M_n$=1.5).

$^1$H NMR (400 MHz, CDCl$_3$); 3.83 (s, C(O)OCH$_3$), 2.0-1.7 (s, C(CH$_3$)), 1.86 (7H, m, CH(CH$_3$)$_2$), 1.1 (CH$_2$C(CH$_3$)(COOCH$_3$)), 0.95 (21H, d, CH(CH$_3$)$_2$), 0.8 (CH$_2$C(CH$_3$)(COOCH$_3$)), 0.60 (14H, SiCH$_2$CH)

$^{19}$F NMR (376 MHz, CDCl$_3$); −81.3 (3F, s, CF$_3$), −114.7 (2F, dd, J=276.0, 670.4 Hz, CH$_2$CF$_2$), −122.3 (2F, s, CF$_2$), −123.4 (2F, s, CF$_2$), −124.1 (2F, s, CF$_2$), −126.6 (2F, s, CF$_2$)

Example 5

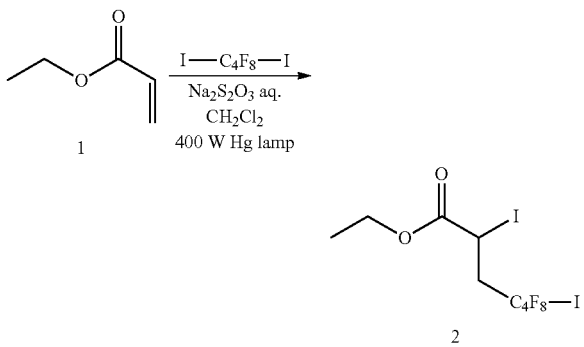

In a Pyrex tube, Compound 1 (20.3 mg) was dissolved in CH$_2$Cl$_2$ (4 ml), I—C$_4$F$_8$—I (36 μL) and an aqueous sodium thiosulfate solution (158 mg, 1 ml aqueous solution) were added thereto, and the mixture was irradiated with ultraviolet ray for 24 hours using a 400 W high-pressure mercury lamp while keeping the temperature of the reaction system constant. The obtained reaction mixture was analyzed by 1H and $^{19}$F NMR to confirm that the desired product was obtained.

$^1$H NMR (400 MHz, CDCl$_3$); 4.6 (1H, dd, 3.8, 10.6 Hz, ICH), 4.2 (2H, OCH$_2$CH$_3$), 3.2 (1H, m, CF$_2$CHH), 2.7 (1H, m, CF$_2$CHH), 1.2 (3H, CH$_2$CH$_3$)

$^{19}$F NMR (376 MHz, CDCl$_3$); −114.8 (2F, dd, J=265.8, 647.1 Hz, CH$_2$CF$_2$), −123.8 (2F, s, CH$_2$CF$_2$CF$_2$), −113.2 (2F, s, CF$_2$CF$_2$I), −59.1 (2F, s, CF$_2$I)

Example 6

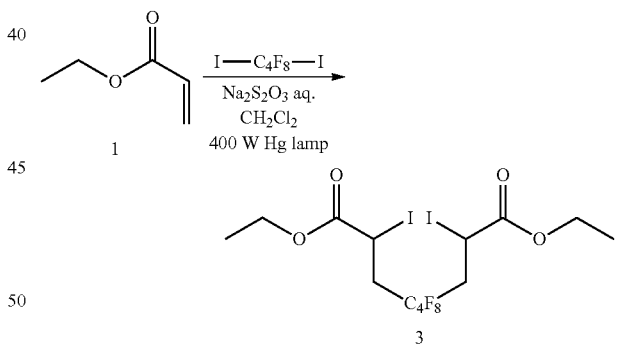

In a Pyrex tube, Compound 1 (60.6 mg) was dissolved in CH$_2$Cl$_2$ (4 ml), I—C$_4$F$_8$—I (36 μL) and an aqueous sodium thiosulfate solution (316 mg, 1 ml aqueous solution) were added thereto, and the mixture was irradiated with ultraviolet ray for 24 hours using a 400 W high-pressure mercury lamp while keeping the temperature of the reaction system constant. The obtained reaction mixture was analyzed by $^1$H and $^{19}$F NMR to confirm that the desired product was obtained.

$^1$H NMR (400 MHz, CDCl$_3$); 4.6 (2H, dd, 3.8, 10.6 Hz, ICH), 4.2 (4H, OCH$_2$CH$_3$), 3.2 (2H, m, CF$_2$CHH), 2.7 (2H, m, CF$_2$CHH), 1.2 (6H, CH$_2$CH$_3$)

$^{19}$F NMR (376 MHz, CDCl$_3$); −114.8 (4F, dd, J=277.5, 658.8 Hz, CH$_2$CF$_2$), −123.1 (4F, s, CF$_2$)

Example 7

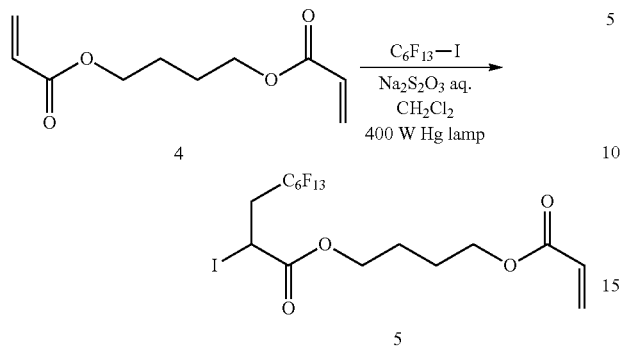

In a Pyrex tube, Compound 4 (39.9 mg) was dissolved in CH$_2$Cl$_2$ (4 ml), C$_6$F$_{13}$—I (44 μL) and an aqueous sodium thiosulfate solution (158 mg, 1 ml aqueous solution) were added thereto, and the mixture was irradiated with ultraviolet ray for 1 hour using a 400 W high-pressure mercury lamp while keeping the temperature of the reaction system constant. The obtained reaction mixture was analyzed by $^1$H and $^{19}$F NMR to confirm that the desired product was obtained.

$^1$H NMR (400 MHz, CDCl$_3$); 6.4 (1H, dd, CH$_2$=CHC(O)), 6.1 (1H, dd, CH$_2$=CHC(O)), 5.8 (1H, dd, CH$_2$=CHC(O)), 4.2 (4H, OCH$_2$), 4.2 (1H, m, ICH), 3.3 (1H, m, CF$_2$CHH), 2.7 (1H, m, CF$_2$CHCH), 1.8 (4H, OCH$_2$CH$_2$)

$^{19}$F NMR (376 MHz, CDCl$_3$); −81.3 (3F, s, CF$_3$), −114.7 (2F, dd, J=276.0, 670.4 Hz, CH$_2$CF$_2$), −122.3 (2F, s, CF$_2$), −123.4 (2F, s, CF$_2$), −124.1 (2F, s, CF$_2$), −126.6 (2F, s, CF$_2$)

Example 8

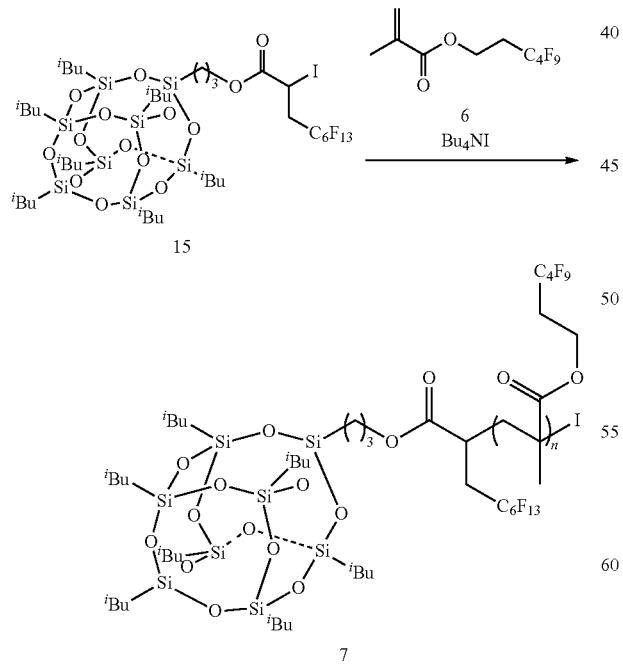

In a reaction vessel, Compound 15 (138 mg) was dissolved in toluene (0.79 mL), Compound 6 (2.36 mL) and tetrabutylammonium iodide (36.7 mg) were added thereto, and the inside of the reaction vessel was sufficiently substituted with an inert gas, followed by heating at 120° C. for 5 hours. After completion of the reaction, the reaction mixture was purified by re-precipitation to give Compound 7 (yield: 27%, M$_n$=3.8×10$^3$, M$_w$/M$_n$=3.5).

$^1$H NMR (400 MHz, C$_6$D$_6$) δ 4.17 (262H, br s), 2.25 (314H, br s), 2.02 (133H, br s), 1.41-1.09 (562H, br m), 1.07 (86H, dt, J=9.2, 3.7 Hz), 0.77 (14H, d, J=6.9 Hz).

$^{19}$F NMR (376 MHz, C$_6$D$_6$) δ −79.38 (3 nF, s), −118.80 (2 nF, dd, J=433.5, 283.2 Hz), −130.20 (2 nF, s), −132.08 (2 nF, s)

Example 9

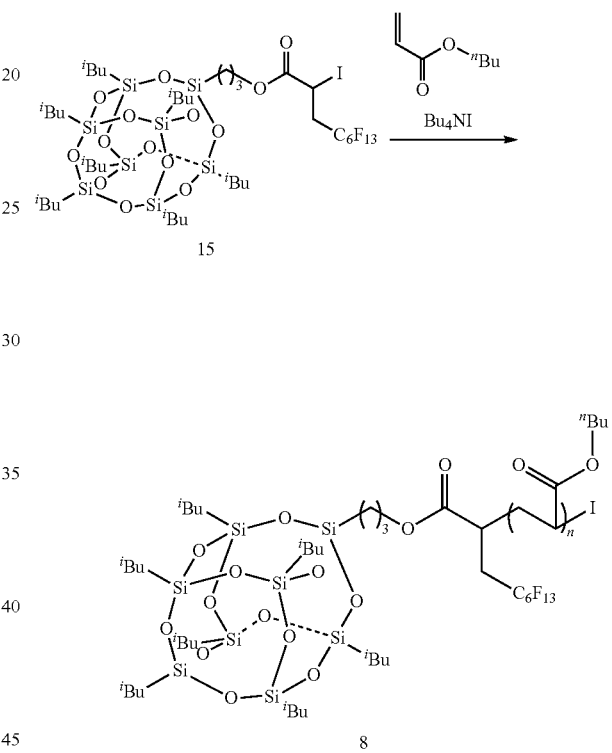

In a reaction vessel, Compound 15 (138 mg), butyl acrylate (1.40 mL) and tetrabutylammonium iodide (one equivalent) were added thereto, and the inside of the reaction vessel was sufficiently substituted with an inert gas, followed by heating at 110° C. for 48 hours. After completion of the reaction, the reaction mixture was purified by re-precipitation to give Compound 8 (yield 34%, M$_n$=7.0×10$^3$, M$_w$/M$_n$=1.24).

$^1$H NMR (400 MHz, CDCl$_3$) δ 4.09-3.96 (53H, m), 2.36-2.28 (23H, br m), 1.92-1.78 (18H, m), 1.67-1.62 (82H, m), 1.49-1.47 (8H, m), 1.37 (55H, dd, J=14.2, 7.3 Hz), 0.96-0.92 (120H, m), 0.60 (14H, t, J=5.7 Hz).

$^{19}$F NMR (376 MHz, CDCl$_3$) δ −81.28 (3F, s), −113.95 (2F, s), −122.34 (2F, s), −123.38 (2F, s), −124.12 (1F, s), −126.64 (2F, s).

Example 10

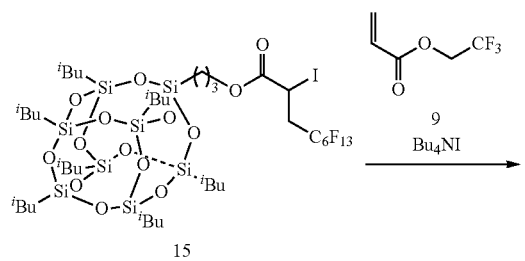

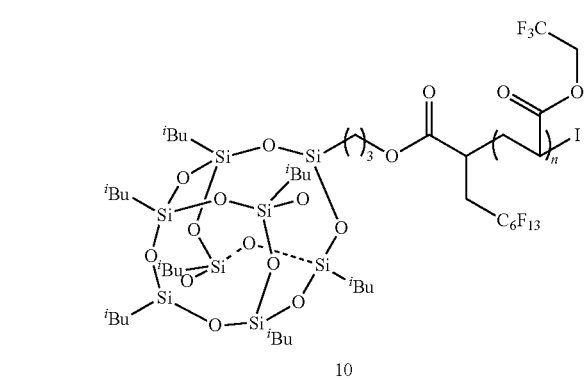

In a reaction vessel, Compound 15 (138 mg), Compound 9 (1.25 mL) and tetrabutylammonium iodide (148 mg) were added thereto, and the inside of the reaction vessel was sufficiently substituted with an inert gas, followed by heating at 110° C. for 48 hours. After completion of the reaction, the reaction mixture was purified by re-precipitation to give Compound 10 (yield 7%, $M_n$=2.3×10$^3$).

$^1$H NMR (400 MHz, CDCl$_3$) δ 4.47 (12H, br s), 2.47 (6H, br s), 2.05 (3H, br s), 1.86 (6H, tt, J=9.8, 4.5 Hz), 1.78 (8H, br s), 1.56 (5H, br s), 0.95 (40H, t, J=6.4 Hz), 0.62-0.59 (14H, m).

$^{19}$F NMR (376 MHz, CDCl$_3$) δ −74.49 (3 nF, s), −81.28 (3F, s), −113.98 (1F, s), −115.30 (1F, s), −121.97--122.60 (2F, m), −123.14--123.78 (2F, m), −123.94--124.40 (1F, m), −126.67 (2F, s).

Example 11

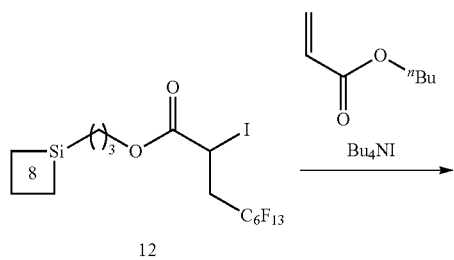

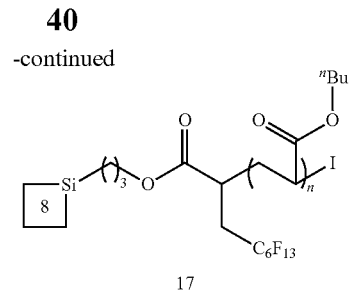

In a reaction vessel, Compound 12 (488 mg), butyl acrylate (2.30 mL) and tetrabutylammonium iodide (147 mg) were added thereto, and the inside of the reaction vessel was sufficiently substituted with an inert gas, followed by heating at 120° C. for 1 hour. After completion of the reaction, the reaction mixture was purified by re-precipitation to give Compound 17 (yield: 10%, $M_n$=3.1×10$^4$, $M_w/M_n$=2.05).

$^{19}$F NMR (376 MHz, CDCl$_3$) δ−81.43 (3F, s), −109.98 (2F, s), −122.5 (2F, s), −123.5 (2F, s), −123.8-125.0 (2F, m), −126.9 (2F, s).

Example 12

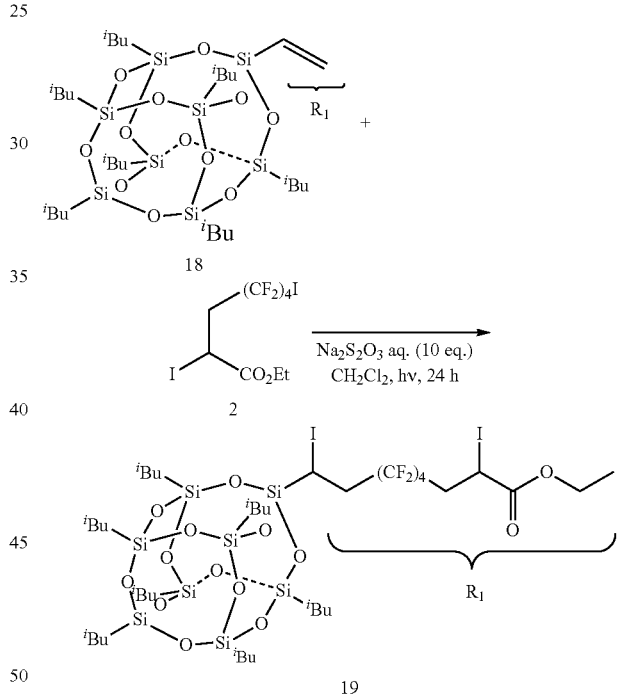

In a Pyrex tube, Compound 18 (168 mg) was dissolved in CH$_2$Cl$_2$ (5.0 ml), Compound 2 (553 mg) and an aqueous sodium thiosulfate solution (317 mg, 1 ml aqueous solution) were added thereto, and the mixture was irradiated with ultraviolet ray for 24 hours using a 400 W high-pressure mercury lamp while keeping the temperature of the reaction system constant. The obtained reaction mixture was analyzed by 1H and $^{19}$F NMR, and it was confirmed that Compound 19 was obtained in 52% yield.

$^1$H NMR (400 MHz, CDCl$_3$); 4.60 (1H, m, CH$_2$CHICO$_2$CH$_2$)), 4.23 (2H, q, CO$_2$CH$_2$CH$_3$), 3.30 (1H, m, CF$_2$CH$_2$CHI), 3.12 (1H, dd, SiCHICH$_2$), 2.88 (1H, m, CF$_2$CH$_2$CHI), 2.80-2.45 (2H, m, SiCHICH$_2$CF$_2$), 1.86 (7H, tq, CH$_2$CH(CH$_3$)$_2$), 1.28 (3H, t, CO$_2$CH$_2$CH$_3$), 0.95 (14H, d, CH$_2$CH(CH$_3$)$_2$), 0.64 (42H, m, SiCH$_2$CH(CH$_3$)$_2$)

$^{19}$F NMR (376 MHz, CDCl$_3$); −115.0 (2F, dd, CH$_2$CF$_2$), −115.6 (2F, dd, CF$_2$CH$_2$) −124.1 (4F, s, CF$_2$CF$_2$CF$_2$CF$_2$)

Example 13

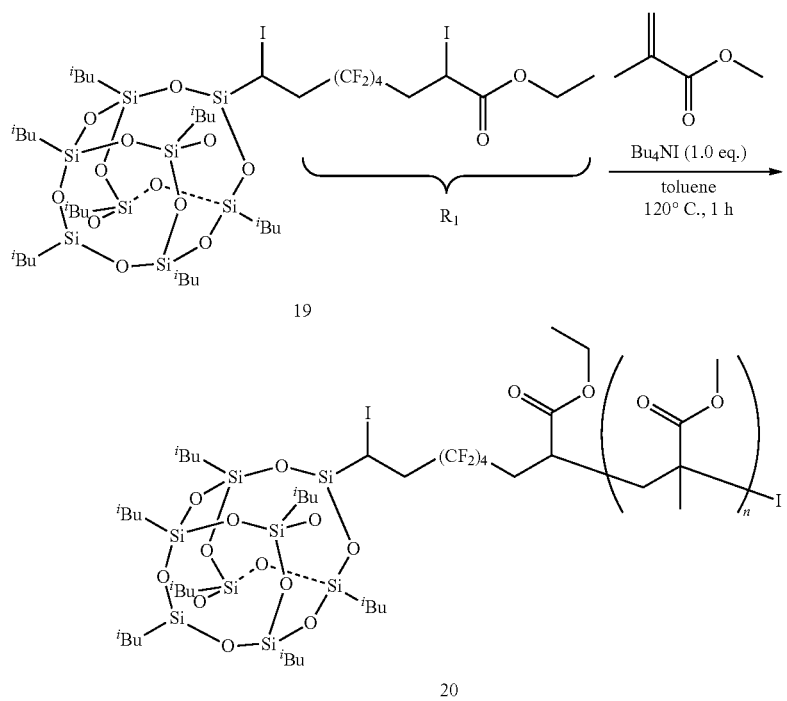

In a reaction vessel, Compound 19 (150 mg) was dissolved in toluene (0.37 mL), methyl methacrylate (1.1 mL) and tetrabutylammonium iodide (36.7 mg) were added thereto, and the inside of the reaction vessel was sufficiently substituted with an inert gas, followed by heating at 120° C. for 1 hour. After completion of the reaction, the reaction mixture was purified by re-precipitation to give Compound 20 (yield: 36%, $M_n$=1.2×10$^4$, $M_w/M_n$=1.15).

$^1$H NMR (400 MHz, CDCl$_3$); 4.14 (2H, q, CO$_2$CH$_2$CH$_3$), 3.60 (3nH, s, CO$_2$CH$_3$), 3.12 (1H, dd, SiCHICH$_2$), 2.65-2.45 (2H, m, SiCHICH$_2$CF$_2$), 2.1-1.7 (br, CH$_2$C(CH$_3$)(CO$_2$CH$_3$)), 1.50-1.35 (br, CH$_2$C(CH$_3$)(CO$_2$CH$_3$)), 1.30-1.18 (br, CH$_2$C(CH$_3$)(CO$_2$CH$_3$)), 1.02 (s, CH$_2$C(CH$_3$)(CO$_2$CH$_3$)), 0.95 (14H, d, SiCH$_2$CH(CH$_3$)$_2$), 0.85 (s, CH$_2$C(CH$_3$)(CO$_2$CH$_3$)), 0.64 (42H, m, SiCH$_2$CH(CH$_3$)$_2$)

$^{19}$F NMR (376 MHz, CDCl$_3$); −114.28 (2F, CH$_2$CF$_2$), −115.6 (2F, CF$_2$CH$_2$), −124.2 (4F, s, CF$_2$CF$_2$CF$_2$CF$_2$)

Example 14

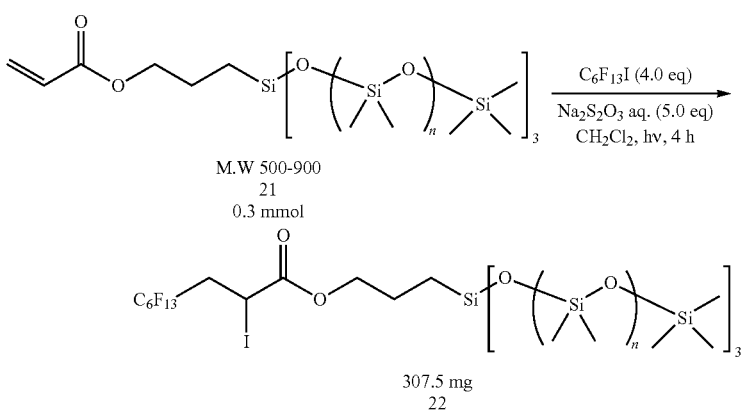

In a Pyrex tube, Compound 21 (210 mg) was dissolved in CH$_2$Cl$_2$ (7.5 ml), C$_6$F$_{13}$I (0.26 mL) and an aqueous sodium thiosulfate solution (237 mg, 1.5 ml aqueous solution) were added thereto, and the mixture was irradiated with ultraviolet ray for 4 hours using a 400 W high-pressure mercury lamp while keeping the temperature of the reaction system constant. The obtained reaction mixture was analyzed by $^1$H and $^{19}$F NMR, and it was confirmed that 308 mg of Compound 22 was obtained.

$^1$H NMR (400 MHz, CDCl$_3$); δ 4.61 (1H, dd, J=12.0, 4.0 Hz), 4.18-4.12 (2H, br m), 3.40-3.22 (1H, m), 2.74-2.63 (1H, m), 1.80-1.62 (2H, br m), 0.70-0.4 (2H, br m), 0.30--0.15 ((6n+9)H, br m)

$^{19}$F NMR (376 MHz, CDCl$_3$); δ−81.3 (3F, s), −114.7 (2F, dd, J=646.7, 278.2 Hz), −122.3 (2F, s), −123.4 (2F, s), −124.1 (2F, s), −126.6 (2F, s)

Example 15

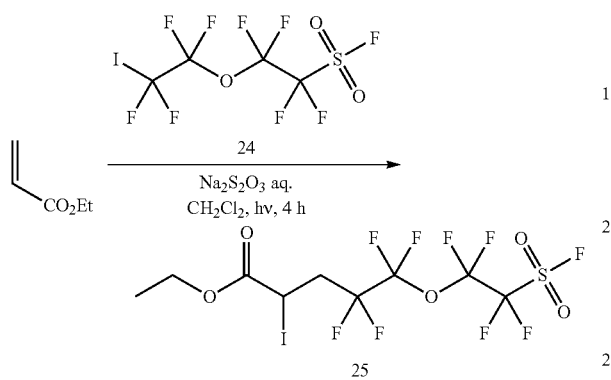

In a Pyrex tube, ethyl acrylate (121 mg) was dissolved in CH$_2$Cl$_2$ (25 ml), Compound 24 (0.21 mL) and an aqueous sodium thiosulfate solution (791 mg, 5 ml aqueous solution) were added thereto, and the mixture was irradiated with ultraviolet ray for 4 hours using a 400 W high-pressure mercury lamp while keeping the temperature of the reaction system constant. The obtained reaction mixture was analyzed by $^1$H and $^{19}$F NMR, and it was confirmed that 271 mg of Compound 25 was obtained.

$^1$H NMR (400 MHz, CDCl$_3$); δ 4.57 (1H, dd, J=10.4, 3.6 Hz), 4.32-4.22

(2H, m), 3.30-3.18 (1H, m), 2.72-2.59 (1H, m), 1.35-1.25 (3H, t, J=7.2 Hz)

$^{19}$F NMR (376 MHz, CDCl$_3$); δ 45.1 (1F, s), −82.6 (2F, s), −88.1 (2F, s), −112.7 (2F, s), −118.43 (2F, dd, J=684.6, 259.6 Hz)

Example 16

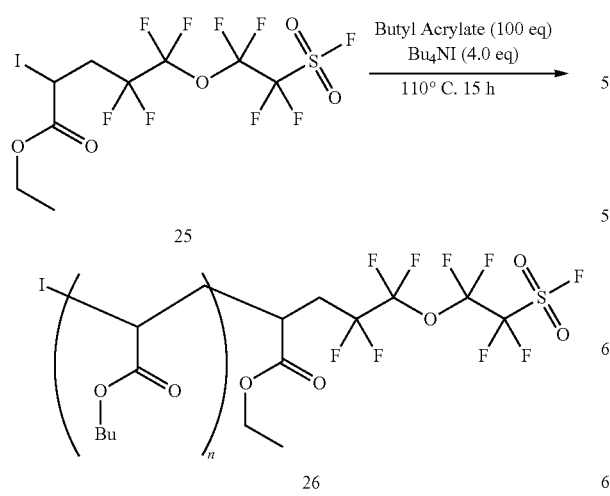

In a reaction vessel, Compound 25 (53 mg), butyl acrylate (1.4 mL) and tetrabutylammonium iodide (148 mg) were added thereto, and the inside of the reaction vessel was sufficiently substituted with an inert gas, followed by heating at 110° C. for 15 hours. After completion of the reaction, the reaction mixture was purified by re-precipitation to give Compound 26 (monomer conversion ratio:33%, M$_n$=6.1×10$^3$, M$_w$/M$_n$=1.08).

$^1$H-NMR (CDCl$_3$) δ: 4.09 ((2n)H, br m), 2.28 ((2n)H, br s), 1.91-1.24 ((5n)H, br m), 1.04-0.92 ((3n)H, br m)

$^{19}$F-NMR (CDCl$_3$) δ: 45.08 (1F, s), −82.66 (2F, s), −88.19 (2F, s), −112.66 (2F, s), −117.82--118.71 (2F, m).

Example 17

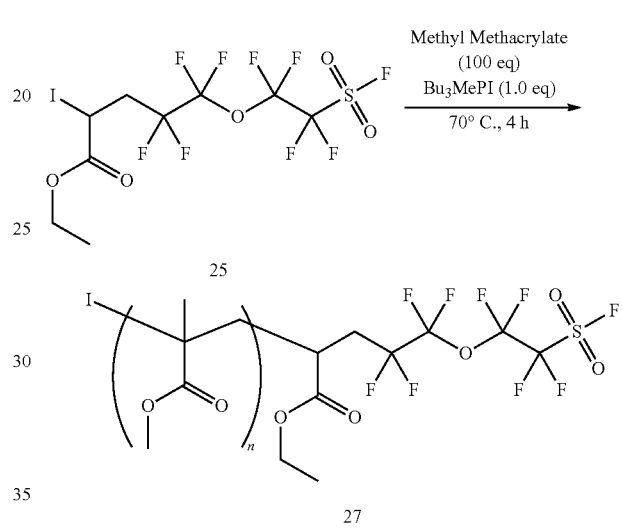

In a reaction vessel, Compound 25 (53 mg) was dissolved in toluene (0.35 mL), methyl methacrylate (1.1 mL) and methyl tributylphosphonium iodide (34.4 mg) were added thereto, and the inside of the reaction vessel was sufficiently substituted with an inert gas, followed by heating at 70° C. for 4 hours. After completion of the reaction, the reaction mixture was purified by re-precipitation to give Compound 27 (monomer conversion ratio:64%, M$_n$=1.2×10$^4$, M$_w$/M$_n$=1.18).

$^1$H-NMR (CDCl$_3$) δ: 3.69 ((3n)H, br s), 2.17-1.81 ((2n)H, br m), 1.02, 0.87 ((3n) H, br s).

$^{19}$F-NMR (CDCl$_3$) δ: 44.90 (1F, s), −82.60 (2F, s), −88.16 (2F, s), −112.66 (2F, s), −118.13 (2F, d, J=69.6 Hz).

INDUSTRIAL APPLICABILITY

The compound of the present disclosure is suitably used as a polymerization initiator.

What is claimed is:
1. A compound represented by formula (3):

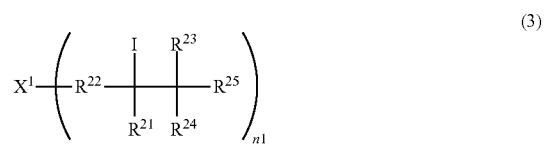

(3)

wherein
$X^1$ is an n1-valent siloxane group;
$R^{21}$ is H, F, Cl, $CH_3$, $CF_3$, or $O(CF_2)_{p3}F$;
$R^{22}$ is $-R^{26}-OCO-$ wherein $R^{26}$ is bonded to $X^1$;
$R^{23}$ is H or F;
$R^{24}$ is H, F, an aryl group, $-COOR^{30}$, or an alkyl group optionally substituted with fluorine;
$R^{25}$ is H, F, an aryl group, $-COOR^{30}$, or an alkyl group optionally substituted with fluorine;
$R^{26}$ is a single bond or an alkylene group optionally substituted with fluorine;
$R^{30}$ is H or an alkyl group;
p3 is an integer of 1 to 10; and
n1 is an integer of 1 to 10,
wherein the siloxane group is represented by the following formula:
$-(SiR^{27}_2-O)_q-SiR^{27}_2-$,
$-SiR^{28}_r R^{29}_{3-r}$, or
$(R^a SiO_{1.5})_t$ wherein
$R^{27}$, each independently at each occurrence, is a hydrogen atom or an alkyl group;
$R^{28}$, each independently at each occurrence, is $-O-(SiR^{27}_2-O)_s-SiR^{27}_3-$;
$R^{29}$ is a single bond;
$R^a$, each independently at each occurrence, is $R^b$ or $R^c$, provided that
at least one $R^a$ is $R^b$,
$R^b$ is a single bond, and
$R^c$ is a hydrogen atom or alkyl;
q is an integer of 1 to 20;
r is an integer of 1 to 3;
s is an integer of 0 to 20; and
t is any integer.

2. A polymerization initiator comprising the compound according to claim 1.

* * * * *